United States Patent
Sato et al.

(10) Patent No.: US 11,752,134 B2
(45) Date of Patent: *Sep. 12, 2023

(54) COMPOSITION FOR ENHANCING COGNITIVE FUNCTION, COMPOSITION FOR REMEDYING ANXIETY SYMPTOMS, AND COMPOSITION FOR SUPPRESSING CEREBRAL ATROPHY

(71) Applicant: AJINOMOTO CO., INC., Tokyo (JP)

(72) Inventors: Hideaki Sato, Kawasaki (JP); Masako Yasui, Kawasaki (JP); Yusuke Adachi, Kawasaki (JP); Katsuya Suzuki, Kawasaki (JP); Michihiro Takada, Kawasaki (JP)

(73) Assignee: AJINOMOTO CO., INC., Tokyo (JP)

(*) Notice: Subject to any disclaimer, the term of this patent is extended or adjusted under 35 U.S.C. 154(b) by 272 days.

This patent is subject to a terminal disclaimer.

(21) Appl. No.: 17/001,776

(22) Filed: Aug. 25, 2020

(65) Prior Publication Data

US 2020/0383952 A1 Dec. 10, 2020

Related U.S. Application Data

(63) Continuation of application No. PCT/JP2019/008715, filed on Mar. 5, 2019.

(30) Foreign Application Priority Data

Mar. 5, 2018 (JP) .................. 2018-038950

(51) Int. Cl.
*A61K 31/4172* (2006.01)
*A61P 25/28* (2006.01)
*A61K 31/198* (2006.01)
*A61K 31/405* (2006.01)

(52) U.S. Cl.
CPC ........ *A61K 31/4172* (2013.01); *A61K 31/198* (2013.01); *A61K 31/405* (2013.01); *A61P 25/28* (2018.01)

(58) Field of Classification Search
USPC ........................................................ 514/400
See application file for complete search history.

(56) References Cited

U.S. PATENT DOCUMENTS

| | | |
|---|---|---|
| 2007/0010437 A1 | 1/2007 | Dioguardi |
| 2007/0286909 A1 | 12/2007 | Smith et al. |
| 2011/0081329 A1 | 4/2011 | Smith et al. |
| 2011/0245313 A1 | 10/2011 | Dioguardi |
| 2013/0108731 A1 | 5/2013 | Scheele |
| 2019/0247347 A1 | 8/2019 | Nishitani |

FOREIGN PATENT DOCUMENTS

| | | |
|---|---|---|
| EP | 2 367 547 A1 | 9/2011 |
| EP | 2 959 895 A1 | 12/2015 |
| EP | 3 357 352 A1 | 8/2018 |
| JP | 2016-210720 A | 12/2016 |
| WO | WO 2005/034932 A2 | 4/2005 |
| WO | WO 2010/068173 A1 | 6/2010 |
| WO | WO 2018/047980 A1 | 3/2018 |

OTHER PUBLICATIONS

International Search Report dated May 7, 2019 in PCT Application No. PCT/JP2019/008715 filed Mar. 5, 2019, 2 pages.
Paolo Rossetti, et al., "Effect of Oral Amino Acids on Counter-regulatory Responses and Cognitive Function During Insulin-Induced Hypoglycemia in Nondiabetic and Type 1 Diabetic People," Diabetes, vol. 57, Jul. 2008, pp. 1905-1917.
Mariangela Rondanelli, et al., "Mild cognitive impairment in elderly and supplementation," Agro Food Industry Hi-Tech, vol. 22, No. 4, 2011, pp. 23-24.
Yoshinori Ohtsuka, et al., "Effect of oral administration of L-arginine on senile dementia," The American Journal of Medicine, vol. 108, Apr. 1, 2000, p. 439.
Robert N Rubey, "Could lysine supplementation prevent Alzheimer's dementia? A novel hypothesis," Neuropsychiatric Disease and Treatment, vol. 6, 2010, pp. 707-710.
Miro Smriga, et al., "Oral treatment with L-lysine and L-arginine reduces anxiety and basal cortisol levels in healthy humans," Biomedical Research, vol. 28, No. 2, 2007, pp. 85-90.
Miro Smriga, et al., "Dietary L-Lysine Deficiency Increases Stress-Induced Anxiety and Fecal Excretion in Rats ," The Journal of Nutrition, vol. 132, 2002, pp. 3744-3746.
Ondine van de Rest, et al., "Literature review on the role of dietary protein and amino acids in cognitive functioning and cognitive decline," Amino Acids, vol. 45, 2013, pp. 1035-1045.
Singaporean Office Action dated Oct. 27, 2021 in Singaporean Patent Application No. 11202008288U, 8 pages.

*Primary Examiner* — Kathrien A Hartsfield
(74) *Attorney, Agent, or Firm* — Oblon, McClelland, Maier & Neustadt, L.L.P.

(57) ABSTRACT

Compositions containing one or more amino acids selected from the group consisting of 25 mol % to 45 mol % of leucine, and 20 mol % to 40 mol % of phenylalanine relative to the total content of leucine, lysine, valine, isoleucine, phenylalanine, histidine, and tryptophan, are useful for improving cognitive function, for improving anxiety-like symptoms, and for suppressing cerebral atrophy and are highly safe and can be ingested or administered continuously.

5 Claims, 5 Drawing Sheets

COMPOSITION FOR ENHANCING COGNITIVE FUNCTION, COMPOSITION FOR REMEDYING ANXIETY SYMPTOMS, AND COMPOSITION FOR SUPPRESSING CEREBRAL ATROPHY

CROSS REFERENCES TO RELATED APPLICATIONS

This application is a continuation of International Patent Application No. PCT/JP2019/008715, filed on Mar. 5, 2019, and claims priority to Japanese Patent Application No. 2018-038950, filed on Mar. 5, 2018, both of which are incorporated herein by reference in their entireties.

BACKGROUND OF THE INVENTION

Field of the Invention

The present invention relates to compositions for improving cognitive function, compositions for improving anxiety-like symptoms, and compositions for suppressing cerebral atrophy. The present invention also relates to methods for improving cognitive function, methods for improving anxiety-like symptoms, and methods for suppressing cerebral atrophy.

Discussion of The Background

With the recent rapid increase in the elderly population, the number of patients with dementia increased rapidly, and it has been reported that the population with dementia reached 8.4% of the population of those aged 65 or over in 2015.

According to the Ministry of Health, Labour and Welfare of Japan, dementia is defined to mean "a state in which various mental functions that once developed normally after the birth have chronically declined and disappeared to the extent that daily life and social life cannot be managed".

Dementia includes dementia caused by various diseases such as Alzheimer-type dementia, frontotemporal dementia (Pick disease etc.), Lewy body dementia, and cerebrovascular dementia. While aging is the greatest risk factor, its cause is often unclear.

However, in any type of dementia, cognitive dysfunction such as memory disorder, disorientation and the like are observed as core symptoms, and behavioral and psychological symptoms such as behavior abnormality, mental symptoms and the like are also commonly observed, and progression of the above-mentioned symptoms has serious effects such as increased burden of nursing care and the like for not only patients but also their families.

Currently, acetylcholinesterase inhibitors such as donepezil hydrochloride, and NMDA (N-methyl-D-aspartate) receptor antagonists such as memantine have been approved as therapeutic drugs for dementia. However, these therapeutic drugs for dementia are basically for Alzheimer-type dementia, are symptomatic treatment drugs, and can merely suppress progression of the symptoms somewhat.

Regarding the prevention of dementia, the importance of meal and exercise in preventing and improving a decline in cognitive function is known.

Regarding meals, the effectiveness of antioxidants such as vitamin C, vitamin E, β-carotene and ω-3 long-chain unsaturated fatty acids has been reported, and the effects of ingestion of ω-3 long-chain unsaturated fatty acid, melatonin and tryptophan on mild cognitive impairment of the elderly people have been studied (see Angro Food Industry Hi-Tech 22 (4) 23-24 (2011), which is incorporated herein by reference in its entirety). Furthermore, there are found a report stating that lysine improves cognitive function of healthy humans (see EP2367547(A1), which is incorporated herein by reference in its entirety), reports suggesting the effect of L-arginine and lysine on Alzheimer-type dementia and anxiety-like symptoms (see The American Journal of Medicine 108 (5) 439 (2000 Apr. 1); Neuropsychiatric Disease and Treatment 6 707-710 (2010); Biomedical Research 28 (2) 85-90 (2007); and The Journal of Nutrition 132 (12) 3744-3746 (2002), all of which are incorporated herein by reference in their entireties), and a report suggesting improvement of a decline in working memory and a decline in cognitive function by tyrosine (see Amino Acids 45 (5) 1035-1045 (2013), which is incorporated herein by reference in its entirety).

Regarding exercise, it has been found that an increase in cerebral blood flow due to exercise can improve physical activity and prevent Alzheimer's disease.

However, some of the above-mentioned ingredients ingested in meals do not have sufficient preventive or improving effect on a decline in cognitive function, and many require future verification of the effectiveness.

Furthermore, some middle-aged and elderly people who have an increased risk of a decline in cognitive function often have difficulty in exercising due to disease or the like, or may have difficulty in continuing exercise due to a decline in physical function.

Therefore, it is difficult to say that a component having an effective preventive or improving effect on the decline in cognitive function, which is highly safe and can be ingested continuously, has been found.

It is known that the proportion of anxiety-like symptoms such as spiritless, apathy, anxiety, depression and the like increases in elderly people, and such anxiety-like symptoms are seen as a risk factor for dementia before the onset of dementia.

Furthermore, it is also known that the above-mentioned anxiety-like symptoms are seen as behavioral and psychological symptoms of dementia.

SUMMARY OF THE INVENTION

Accordingly, it is one object of the present invention to provide novel compositions for improving cognitive function, which have an effective preventive or improving effect on a decline in cognitive function, are highly safe, and enable continuous ingestion or administration.

It is another object of the present invention to provide novel compositions for improving anxiety-like symptoms mentioned above.

It is another object of the present invention to provide novel methods for improving cognitive function, which have an effective preventive or improving effect on a decline in cognitive function, are highly safe, and enable continuous ingestion or administration.

It is another object of the present invention to provide novel methods for improving anxiety-like symptoms mentioned above.

These and other objects, which will become apparent during the following detailed description, have been achieved by the inventors' discovery that a composition containing one or more kinds selected from the group consisting of 25 mol % to 45 mol % of leucine, and 20 mol % to 40 mol % of phenylalanine relative to the total content of leucine, lysine, valine, isoleucine, phenylalanine, histidine and tryptophan has an improving effect of cognitive function and an improving effect of anxiety-like symptoms, and that the aforementioned composition has an effect of suppressing cerebral atrophy characteristically observed in neurodegenerative diseases such as Alzheimer-type dementia and the like.

That is, the present invention provides to the following.

(1) A composition for improving cognitive function, comprising one or more kinds selected from the group consisting of 25 mol % to 45 mol % of leucine, and 20 mol % to 40 mol % of phenylalanine relative to the total content of leucine, lysine, valine, isoleucine, phenylalanine, histidine and tryptophan.

(2) The composition of (1), further comprising 10 mol % to 30 mol % of lysine relative to the total content of leucine, lysine, valine, isoleucine, phenylalanine, histidine and tryptophan.

(3) The composition of (1) or (2), further comprising one or more kinds selected from the group consisting of valine, isoleucine, histidine and tryptophan.

(4) The composition of (3), comprising one or more kinds selected from the group consisting of 2 mol % to 7 mol % of valine, 5 mol % to 15 mol % of isoleucine, 2 mol % to 10 mol % of histidine and 0.1 mol % to 2 mol % of tryptophan relative to the total content of leucine, lysine, valine, isoleucine, phenylalanine, histidine and tryptophan.

(5) The composition of (3) or (4), comprising the following amino acids at the following contents relative to the total content of leucine, lysine, valine, isoleucine, phenylalanine, histidine and tryptophan:
　leucine 25 mol % to 45 mol %,
　phenylalanine 20 mol % to 40 mol %,
　lysine 10 mol % to 30 mol %,
　valine 2 mol % to 7 mol %,
　isoleucine 5 mol % to 15 mol %,
　histidine 2 mol % to 10 mol %, and
　tryptophan 0.1 mol % to 2 mol %.

(6) The composition of any of (1) to (5), wherein the composition is a pharmaceutical product.

(7) The composition of any of (1) to (5), wherein the composition is a food.

(8) A method for improving cognitive function of a subject animal in need of improving cognitive function, comprising allowing the animal to ingest a composition comprising one or more kinds selected from the group consisting of 25 mol % to 45 mol % of leucine, and 20 mol % to 40 mol % of phenylalanine relative to the total content of leucine, lysine, valine, isoleucine, phenylalanine, histidine and tryptophan, in an amount effective for improving cognitive function of the subject animal, or administering said amount of the composition to the subject animal.

(9) The method of (8), wherein the composition further comprising 10 mol % to 30 mol % of lysine relative to the total content of leucine, lysine, valine, isoleucine, phenylalanine, histidine and tryptophan.

(10) The method of (8) or (9), wherein the composition further comprising one or more kinds selected from the group consisting of valine, isoleucine, histidine and tryptophan.

(11) The method of (10), wherein the composition comprising one or more kinds selected from the group consisting of 2 mol % to 7 mol % of valine, 5 mol % to 15 mol % of isoleucine, 2 mol % to 10 mol % of histidine and 0.1 mol % to 2 mol % of tryptophan relative to the total content of leucine, lysine, valine, isoleucine, phenylalanine, histidine and tryptophan.

(12) The method of (10) or (11), wherein the composition comprising the following amino acids at the following contents relative to the total content of leucine, lysine, valine, isoleucine, phenylalanine, histidine and tryptophan:
　leucine 25 mol % to 45 mol %,
　phenylalanine 20 mol % to 40 mol %,
　lysine 10 mol % to 30 mol %,
　valine 2 mol % to 7 mol %,
　isoleucine 5 mol % to 15 mol %,
　histidine 2 mol % to 10 mol %, and
　tryptophan 0.1 mol % to 2 mol %.

(13) A composition for improving an anxiety-like symptom, comprising one or more kinds selected from the group consisting of 25 mol % to 45 mol % of leucine, and 20 mol % to 40 mol % of phenylalanine relative to the total content of leucine, lysine, valine, isoleucine, phenylalanine, histidine and tryptophan.

(14) The composition of (13), further comprising 10 mol % to 30 mol % of lysine relative to the total content of leucine, lysine, valine, isoleucine, phenylalanine, histidine and tryptophan.

(15) The composition of (13) or (14), further comprising one or more kinds selected from the group consisting of valine, isoleucine, histidine and tryptophan.

(16) The composition of (15), comprising one or more kinds selected from the group consisting of 2 mol % to 7 mol % of valine, 5 mol % to 15 mol % of isoleucine, 2 mol % to 10 mol % of histidine and 0.1 mol % to 2 mol % of tryptophan relative to the total content of leucine, lysine, valine, isoleucine, phenylalanine, histidine and tryptophan.

(17) The composition of (15) or (16), comprising the following amino acids at the following contents relative to the total content of leucine, lysine, valine, isoleucine, phenylalanine, histidine and tryptophan:
　leucine 25 mol % to 45 mol %,
　phenylalanine 20 mol % to 40 mol %,
　lysine 10 mol % to 30 mol %,
　valine 2 mol % to 7 mol %,
　isoleucine 5 mol % to 15 mol %,
　histidine 2 mol % to 10 mol %, and
　tryptophan 0.1 mol % to 2 mol %.

(18) The composition of any of (13) to (17), wherein the composition is a pharmaceutical product.

(19) The composition of any of (13) to (17), wherein the composition is a food.

(20) A method for improving an anxiety-like symptom of a subject animal in need of improving an anxiety-like symptom, comprising allowing the animal to ingest a composition comprising one or more kinds selected from the group consisting of 25 mol % to 45 mol % of leucine, and 20 mol % to 40 mol % of phenylalanine relative to the total content of leucine, lysine, valine, isoleucine, phenylalanine, histidine and tryptophan, in an amount effective for improving the anxiety-like symptom of the subject animal, or administering said amount of the composition to the subject animal.

(21) The method of (20), wherein the composition further comprising 10 mol % to 30 mol % of lysine relative to the total content of leucine, lysine, valine, isoleucine, phenylalanine, histidine and tryptophan.

(22) The method of (20) or (21), wherein the composition further comprising one or more kinds selected from the group consisting of valine, isoleucine, histidine and tryptophan.

(23) The method of (22), wherein the composition comprising one or more kinds selected from the group consisting of 2 mol % to 7 mol % of valine, 5 mol % to 15 mol % of isoleucine, 2 mol % to 10 mol % of histidine and 0.1 mol % to 2 mol % of tryptophan relative to the total content of leucine, lysine, valine, isoleucine, phenylalanine, histidine and tryptophan.

(24) The method of (22) or (23), wherein the composition comprising the following amino acids at the following contents relative to the total content of leucine, lysine, valine, isoleucine, phenylalanine, histidine and tryptophan:
  leucine 25 mol % to 45 mol %,
  phenylalanine 20 mol % to 40 mol %,
  lysine 10 mol % to 30 mol %,
  valine 2 mol % to 7 mol %,
  isoleucine 5 mol % to 15 mol %,
  histidine 2 mol % to 10 mol %, and
  tryptophan 0.1 mol % to 2 mol %.

(25) A composition for suppressing cerebral atrophy, comprising one or more kinds selected from the group consisting of 25 mol % to 45 mol % of leucine, and 20 mol % to 40 mol % of phenylalanine relative to the total content of leucine, lysine, valine, isoleucine, phenylalanine, histidine and tryptophan.

(26) The composition of (25), further comprising 10 mol % to 30 mol % of lysine relative to the total content of leucine, lysine, valine, isoleucine, phenylalanine, histidine and tryptophan.

(27) The composition of (25) or (26), further comprising one or more kinds selected from the group consisting of valine, isoleucine, histidine and tryptophan.

(28) The composition of (27), comprising one or more kinds selected from the group consisting of 2 mol % to 7 mol % of valine, 5 mol % to 15 mol % of isoleucine, 2 mol % to 10 mol % of histidine and 0.1 mol % to 2 mol % of tryptophan relative to the total content of leucine, lysine, valine, isoleucine, phenylalanine, histidine and tryptophan.

(29) The composition of (27) or (28), comprising the following amino acids at the following contents relative to the total content of leucine, lysine, valine, isoleucine, phenylalanine, histidine and tryptophan:
  leucine 25 mol % to 45 mol %,
  phenylalanine 20 mol % to 40 mol %,
  lysine 10 mol % to 30 mol %,
  valine 2 mol % to 7 mol %,
  isoleucine 5 mol % to 15 mol %,
  histidine 2 mol % to 10 mol %, and
  tryptophan 0.1 mol % to 2 mol %.

(30) The composition of any of (25) to (29), wherein the composition is a pharmaceutical product.

(31) The composition of any of (25) to (29), wherein the composition is a food.

(32) A method for suppressing cerebral atrophy of a subject animal in need of suppressing cerebral atrophy, comprising allowing the animal to ingest a composition comprising one or more kinds selected from the group consisting of 25 mol % to 45 mol % of leucine, and 20 mol % to 40 mol % of phenylalanine relative to the total content of leucine, lysine, valine, isoleucine, phenylalanine, histidine and tryptophan, in an amount effective for suppressing cerebral atrophy of the subject animal, or administering said amount of the composition to the subject animal.

(33) The method of (32), wherein the composition further comprising 10 mol % to 30 mol % of lysine relative to the total content of leucine, lysine, valine, isoleucine, phenylalanine, histidine and tryptophan.

(34) The method of (32) or (33), wherein the composition further comprising one or more kinds selected from the group consisting of valine, isoleucine, histidine and tryptophan.

(35) The method of (34), wherein the composition comprising one or more kinds selected from the group consisting of 2 mol % to 7 mol % of valine, 5 mol % to 15 mol % of isoleucine, 2 mol % to 10 mol % of histidine and 0.1 mol % to 2 mol % of tryptophan relative to the total content of leucine, lysine, valine, isoleucine, phenylalanine, histidine and tryptophan.

(36) The method of (34) or (35), wherein the composition comprising the following amino acids at the following contents relative to the total content of leucine, lysine, valine, isoleucine, phenylalanine, histidine and tryptophan:
  leucine 25 mol % to 45 mol %,
  phenylalanine 20 mol % to 40 mol %,
  lysine 10 mol % to 30 mol %,
  valine 2 mol % to 7 mol %,
  isoleucine 5 mol % to 15 mol %,
  histidine 2 mol % to 10 mol %, and
  tryptophan 0.1 mol % to 2 mol %.

Effects of the Invention

The present invention can provide a composition for improving cognitive function that can effectively prevent or improve a decline in cognitive function.

Also, the present invention can provide a composition for improving anxiety-like symptoms. The composition for improving anxiety-like symptoms of the present invention is particularly effective for the improvement of anxiety-like symptoms that appear along with a decline in cognitive function or before and after a decline in cognitive function.

Furthermore, the present invention can provide a composition for suppressing cerebral atrophy. The composition for suppressing cerebral atrophy of the present invention suppresses cerebral atrophy observed in neurodegenerative diseases such as Alzheimer-type dementia and the like, and physiological cerebral atrophy that appears and progresses with aging, and can improve a decline in cognitive function caused by cerebral atrophy.

Particularly, the composition for improving cognitive function, the composition for improving anxiety-like symptoms, and the composition for suppressing cerebral atrophy of the present invention are highly safe and suitable for continuous ingestion or administration.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
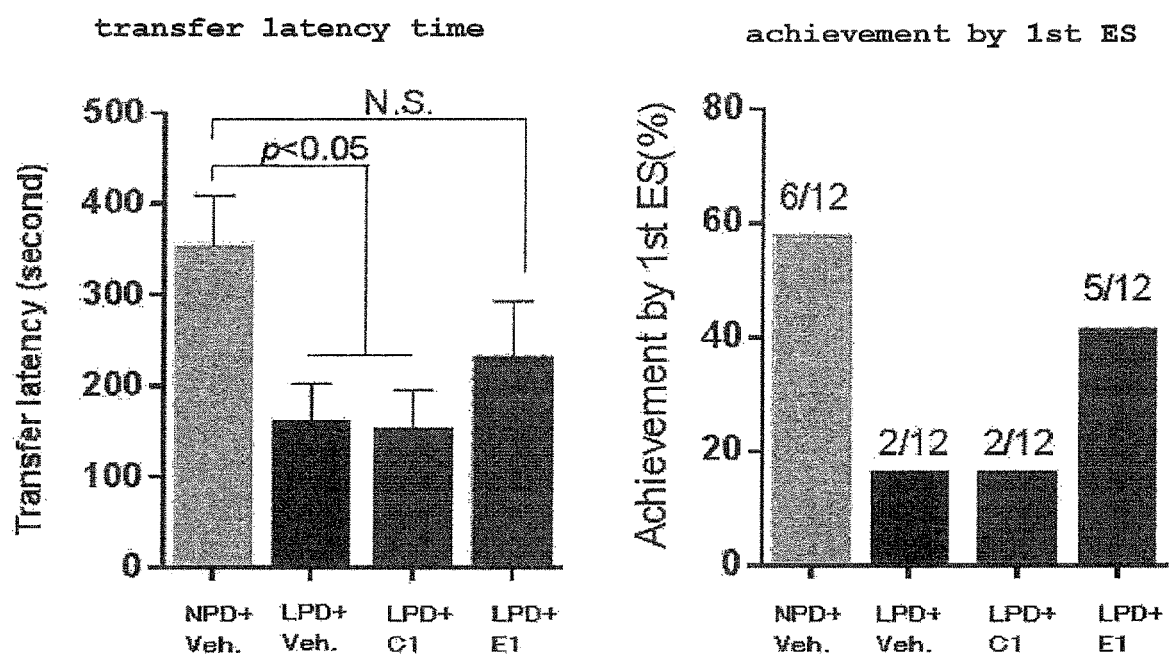
FIG. 1 shows the effects of the composition of Example 1 of the present invention on transfer latency time and achievement by 1st ES in the passive avoidance test in Experimental Example 1. In the Figure, "N.S." indicates no significant difference at critical rate (p)=5%.

The composition for improving cognitive function of the present invention (hereinafter to be also referred to as "the composition of the present invention" in the present specification) contains one or more kinds selected from the group consisting of 25 mol % to 45 mol % of leucine, and 20 mol % to 40 mol % of phenylalanine relative to the total content of leucine, lysine, valine, isoleucine, phenylalanine, histidine and tryptophan (hereinafter to be also referred to as "seven amino acids" in the present specification), that is, one or both of 25 mol % to 45 mol % of leucine, and 20 mol % to 40 mol % of phenylalanine relative to the total content of seven amino acids.

As used herein, the "cognitive function" in the present specification refers to higher-order functions of the brain, such as memory, judgment, calculation, comprehension, learning, thinking, language, performance, attention, orientation, execution, delayed recall and the like, and "improvement of cognitive function" refers to prevention or improvement of a decline in such cognitive function.

The decline in the cognitive function that may be improved by the composition of the present invention includes a decline in cognitive function due to Alzheimer-type dementia, and dementia caused by various diseases and lesions such as frontotemporal lobar degeneration (Pick disease etc.), Lewy body disease, cerebrovascular diseases and the like, a decline in cognitive function due to aging, a decline in cognitive function observed in healthy humans, for example, memory decline, reduction in attention, a decline in thinking skills and the like.

The "leucine" and "phenylalanine" to be used may be any of an L form, a D form and a DL form. An L form and a DL form are preferably used, and an L form is more preferably used.

The "leucine" and "phenylalanine" can be used not only in a free form but also a salt form. The term "leucine" and "phenylalanine" in the present specification are concepts each encompassing even a salt. The salt form is not particularly limited as long as it is a pharmacologically acceptable salt, and acid addition salt, salt with base and the like can be mentioned.

Concrete examples include salts with inorganic bases, salts with organic bases, salts with inorganic acids, salts with organic acids, salts with amino acid and the like.

Examples of the salts with inorganic bases include salts with alkali metals such as lithium, sodium, potassium and the like, salts with alkaline earth metals such as magnesium, calcium and the like, ammonium salt and the like.

Examples of the salts with organic bases include salts with alkanolamine such as monoethanolamine, diethanolamine, triethanolamine and the like, salts with heterocyclic amine such as morpholine, piperidine and the like, and the like.

Examples of the salts with inorganic acids include salts with hydrohalic acid (hydrochloric acid, hydrobromic acid, hydroiodic acid etc.), sulfuric acid, nitric acid, phosphoric acid and the like.

Examples of the salts with organic acids include salts with monocarboxylic acid such as formic acid, acetic acid, propanoic acid and the like; salts with saturated dicarboxylic acid such as oxalic acid, malonic acid, malic acid, succinic acid and the like; salts with unsaturated dicarboxylic acid such as maleic acid, fumaric acid and the like; salts with tricarboxylic acid such as citric acid and the like; salts with keto acid such as α-ketoglutaric acid and the like.

Examples of the salts with amino acid include salts with aliphatic amino acid such as glycine, alanine and the like; salts with aromatic amino acid such as tyrosine and the like; salts with basic amino acid such as arginine and the like; salts with acidic amino acid such as aspartic acid, glutamic acid and the like; salts with amino acid forming lactam such as pyroglutamic acid and the like.

Each of the above-mentioned salts may be a hydrate (salt hydrate), and examples of the hydrate include 1 hydrate to 6 hydrate and the like.

In the present invention, one kind each of "leucine" and "phenylalanine" in the above-mentioned free form or salt form may be used singly, or two or more kinds thereof may be used in combination.

For the object of the present invention, a free form, hydrochloride and the like of each of "leucine" and "phenylalanine" are preferable.

In the composition of the present invention, the content of leucine relative to the total content of seven amino acids is 25 mol % to 45 mol %, preferably 30 mol % to 40 mol %, more preferably 35 mol % to 40 mol %.

In addition, the content of phenylalanine is 20 mol % to 40 mol %, preferably 20 mol % to 35 mol %, more preferably 25 mol % to 30 mol %.

From the aspect of the cognitive function improving effect, the composition of the present invention preferably contains 25 mol % to 45 mol % of leucine and 20 mol % to 40 mol % of phenylalanine.

The composition of the present invention may contain 10 mol % to 30 mol % of lysine relative to the total content of seven amino acids in addition to one or more kinds selected from the group consisting of 25 mol % to 45 mol % of leucine, and 20 mol % to 40 mol % of phenylalanine relative to the total content of seven amino acids.

The "lysine" may be any of an L form, a D form and a DL form, as in the case of the above-mentioned leucine etc. An L form and a DL form are preferably used, and an L form is more preferably used.

The "lysine" can be used not only in a free form but also a salt form, and it is a concept encompassing even a salt.

Examples of the salt form include salts with inorganic bases, salts with organic bases, salts with inorganic acids, salts with organic acids, salts with amino acid and the like as mentioned above.

For the purpose of the present invention, a free form, hydrochloride or the like of "lysine" is preferable.

In the composition of the present invention, the content of lysine relative to the total content of seven amino acids is 10 mol % to 30 mol %, preferably 15 mol % to 25 mol %, more preferably 15 mol % to 20 mol %.

From the aspect of the cognitive function improving effect, the composition of the present invention more preferably contains 25 mol % to 45 mol % of leucine, 20 mol % to 40 mol % of phenylalanine, and 10 mol % to 30 mol % of lysine relative to the total content of seven amino acids.

The composition of the present invention may further contain one or more kinds selected from the group consisting of valine, isoleucine, histidine and tryptophan, in addition to one or more kinds selected from the group consisting of leucine and phenylalanine at the above-mentioned molar composition ratio, or one or more kinds selected from the group consisting of leucine and phenylalanine, and lysine at the above-mentioned molar composition ratio.

The "valine", "isoleucine", "histidine" and "tryptophan" may be any of an L form, a D form and a DL form, as in the case of the above-mentioned leucine etc. An L form and a DL form are preferably used, and an L form is more preferably used.

Each of "valine", "isoleucine", "histidine" and "tryptophan" can be used not only in a free form but also a salt form, and each is a concept encompassing even a salt. Examples of the salt form include salts with inorganic bases, salts with organic bases, salts with inorganic acids, salts with organic acids, salts with amino acid and the like as mentioned above.

For the purpose of the present invention, a free form, hydrochloride or the like of each of "valine", "isoleucine", "histidine" and "tryptophan" is preferable.

The composition of the present invention preferably contains 2 mol % to 7 mol %, more preferably 4 mol % to 6 mol %, of valine relative to the total content of seven amino acids.

Isoleucine is preferably contained at 5 mol % to 15 mol %, more preferably 7 mol % to 13 mol %, relative to the total content of seven amino acids.

Histidine is preferably contained at 2 mol % to 10 mol %, more preferably 2.5 mol % to 8 mol %, relative to the total content of seven amino acids.

Tryptophan is preferably contained at 0.1 mol % to 2 mol %, more preferably 0.3 mol % to 1 mol %, relative to the total content of seven amino acids.

From the aspect of the cognitive function improving effect, the composition of the present invention more preferably contains 25 mol % to 45 mol % of leucine, 20 mol % to 40 mol % of phenylalanine, and 10 mol % to 30 mol % of lysine, as well as 2 mol % to 7 mol % of valine, 5 mol % to 15 mol % of isoleucine, 2 mol % to 10 mol % of histidine and 0.1 mol % to 2 mol % of tryptophan, relative to the total content of seven amino acids.

In the present invention, the above-mentioned each amino acid in a free form or salt form to be used may be extracted from animals, plants or the like, which are naturally present, and purified, or obtained by a chemical synthesis method, a fermentation method, an enzyme method or a gene recombinant method and the like. Commercially available products provided by each company may also be utilized.

The composition of the present invention may further contain, in addition to the above-mentioned amino acids, other nutrition components such as carbohydrates, lipid, protein, essential amino acid (methionine, threonine) other than the above-mentioned amino acid, non-essential amino acid, vitamin, mineral and the like.

The composition of the present invention can be formulated into various forms such as liquids (e.g., solution, suspension, emulsion and the like); semi-solid (e.g., gel, cream and the like); solid (e.g., powder, granule, tablet, capsule and the like), and the like by adding 10 mol % to 30 mol % of lysine, or further, one or more kinds selected from the group consisting of valine, isoleucine, histidine and tryptophan, other nutrition components, pharmaceutically acceptable additives, and the like to one or more kinds selected from the group consisting of 25 mol % to 45 mol % of leucine, and 20 mol % to 40 mol % of phenylalanine relative to the total content of seven amino acids, as necessary and according to a formulating means well known in the field of preparations, for example, the methods described in the Japanese Pharmacopoeia XVII General Rules for preparations [3] Monographs for Preparations, which is incorporated herein by reference in its entirety, and the like.

The above-mentioned pharmaceutically acceptable additive can be appropriately selected according to the form of the composition of the present invention and, for example, excipient, binder, disintegrant, lubricant, coating agent, base, solvent, solubilizing agents, solubilizer, emulsifier, dispersing agent, suspending agent, stabilizer, thickener, soothing agent, isotonicity agent, pH adjuster, antioxidant, antiseptic, preservative, corrigent, sweetener, flavor, colorant and the like can be mentioned.

To be specific, examples of the excipient include magnesium carbonate, saccharides (glucose, lactose, cornstarch etc.), sugar alcohol (sorbitol, mannitol etc.) and the like.

Examples of the binder include gelatin, pregelatinized starch, partly pregelatinized starch, cellulose and a derivative thereof (crystalline cellulose, hydroxypropylcellulose etc.) and the like.

Examples of the disintegrant include crospovidone, povidone, crystalline cellulose and the like.

Examples of the lubricant include talc, magnesium stearate and the like.

Examples of the coating agent include methacrylic acid-methyl methacrylate copolymer, methacrylic acid-ethyl acrylate copolymer, methyl methacrylate-butyl methacrylate-dimethylaminoethyl methacrylate copolymer, ethyl acrylate-methyl methacrylate-trimethylammonioethylmethacrylate chloride copolymer and the like.

Examples of the base include animal and plant fats and oils (olive oil, cacao butter, beef tallow, sesame oil, hydrogenated oil, castor oil etc.), wax (Carnauba wax, beeswax etc.), polyethylene glycol and the like.

Examples of the solvent include purified water, water for injection, monovalent alcohol (ethanol etc.), polyhydric alcohol (glycerol etc.) and the like.

Examples of the solubilizing agent include propylene glycol, medium-chain triglyceride and the like.

Examples of the solubilizer, emulsifier, dispersing agent and suspending agent include surfactant and the like such as sorbitan fatty acid ester, glycerol fatty acid ester, polyoxyethylene sorbitan fatty acid ester (polysorbate 20, polysorbate 80 etc.), polyoxyethylene hydrogenated castor oil, sucrose fatty acid ester and the like.

Examples of the stabilizer include adipic acid, β-cyclodextrin, ethylenediamine, sodium edetate and the like.

Examples of the thickener include water-soluble polymer (sodium polyacrylate, carboxyvinyl polymer etc.), polysaccharides (sodium alginate, xanthan gum, tragacanth etc.) and the like.

Examples of the soothing agent include ethyl aminobenzoate, chlorobutanol, propylene glycol, benzyl alcohol and the like.

Examples of the isotonicity agent include potassium chloride, sodium chloride, sorbitol, saline and the like.

Examples of the pH adjuster include hydrochloric acid, sulfuric acid, acetic acid, citric acid, lactic acid, sodium hydroxide, potassium hydroxide and the like.

Examples of the antioxidant include dibutylhydroxytoluene (BHT), butylhydroxyanisole (BHA), dl-α-tocopherol, erythorbic acid and the like.

Examples of the antiseptic and preservative include paraben (methylparaben etc.), benzyl alcohol, sodium dehydroacetate, sorbic acid and the like.

Examples of the corrigent include ascorbic acid, erythritol, sodium L-glutamate and the like.

Examples of the sweetener include aspartame, licorice extract, saccharin and the like.

Examples of the flavor include 1-menthol, d-camphor, vanillin and the like.

Examples of the colorant include tar pigment (Food Color Red No. 2, Food Color Blue No. 1, Food Color yellow No. 4 etc.), inorganic pigment (red iron oxide, yellow iron oxide, black iron oxide etc.), natural dye (turmeric extract, β-carotene, sodium copper-chlorophyllin etc.) and the like.

In the present invention, one or more kinds of the above-mentioned additives can be used.

The content of "one or more kinds selected from the group consisting of leucine and phenylalanine", "one or more kinds selected from the group consisting of leucine and phenylalanine, and lysine", "one or more kinds selected from the group consisting of leucine and phenylalanine, and one or more kinds selected from the group consisting of valine, isoleucine, histidine and tryptophan", or "one or more kinds selected from the group consisting of leucine and phenylalanine, lysine, and one or more kinds selected from the group consisting of valine, isoleucine, histidine and tryptophan" in the composition of the present invention is generally 30 wt % to 100 wt %, preferably 50 wt % to 100 wt %, relative to the total amount of the composition.

The above-mentioned content of "one or more kinds selected from the group consisting of leucine and phenylalanine" and the like is calculated as a content of the amino acid converted to a free form when any amino acid is contained in the form of a salt.

The composition of the present invention has an effect of improving anxiety-like symptoms in addition to the cognitive function improving effect, and can also be provided as a composition for improving such anxiety-like symptoms.

As used herein, the "anxiety-like symptoms" refers to symptoms such as spiritless, apathy, depressive symptoms (anxiety, depression etc.), restlessness, sleep disorder due to anxiety, excitatory symptoms (agitation, attention deficit, hyperactivity, abnormal behavior etc.) and the like.

The "improvement of anxiety-like symptoms" refers to preventing the expression of the above-mentioned anxiety-like symptoms or reducing the symptoms.

The composition of the present invention is effective for the improvement of the above-mentioned anxiety-like symptoms that appear along with a decline in cognitive function or before and after a decline in cognitive function, namely, anxiety-like symptoms that appear before the onset of dementia and are known as a risk factor for dementia, and anxiety-like symptoms observed as behavioral and psychological symptoms of dementia.

In addition, the composition of the present invention has an effect of suppressing cerebral atrophy, and can also be provided as a composition for suppressing cerebral atrophy.

As used herein, "cerebral atrophy" refers to cerebral atrophy characteristically observed in patients with neurodegenerative diseases such as Alzheimer-type dementia, frontotemporal dementia and the like, and physiological cerebral atrophy observed with aging.

The "suppression of cerebral atrophy" refers to suppression of cerebral atrophy that progresses due to the above-mentioned neurodegenerative diseases and the physiological cerebral atrophy observed with aging.

The composition of the present invention can suppress cerebral atrophy caused by the loss of nerve cells in the above-mentioned neurodegenerative diseases, and can improve a decline in cognitive function caused by such cerebral atrophy. In addition, the composition can also suppress physiological cerebral atrophy that appears and progresses along with aging, and can improve a decline in cognitive function due to such physiological cerebral atrophy, for example, memory decline, reduction in attention, a decline in thinking skills and the like observed in healthy humans along with aging.

The daily ingestion amount or dose of the composition of the present invention is appropriately determined according to the sex, age of the subject to be applied to (hereinafter to be also referred to as the "application subject" in the present specification), conditions such as a decline in cognitive function, and intracerebral lesion and the like observed in the application subject or the state of anxiety-like symptoms and their degree, the form of the composition of the present invention, the administration method and the like. When application subject is a human adult, it is generally 0.5 g to 22 g, preferably 1 g to 20 g, more preferably 2.5 g to 16 g, further preferably 3 g to 16 g, still more preferably 5 g to 16 g, as the total amount of one or more kinds selected from the group consisting of leucine and phenylalanine (i.e., either or both of leucine and phenylalanine) (the total amount converted to the amount of free form), the total amount of either or both of leucine and phenylalanine, and lysine (the total amount converted to the amount of free form), the total amount of either or both of leucine and phenylalanine, and one or more kinds selected from the group consisting of valine, isoleucine, histidine and tryptophan (the total amount converted to the amount of free form), or the total amount of either or both of leucine and phenylalanine, lysine, and one or more kinds selected from the group consisting of valine, isoleucine, histidine and tryptophan (the total amount converted to the amount of free form).

The above-mentioned amount can be ingested or administered at once or in several portions (e.g., 2 to 4 portions) per day.

From the aspect of effectively increasing the blood concentration of the application subject to enhance the cognitive function improving effect, a single ingestion amount or dose of the composition when the application subject is a human adult is generally 0.3 g to g, preferably 0.5 g to 10 g, more preferably 1 g to 8 g, further preferably 2 g to 6 g, still more preferably 2.5 g to 6 g, as the total amount of one or more kinds selected from the group consisting of leucine and phenylalanine (i.e., either or both of leucine and phenylalanine) (the total amount converted to the amount of free form), the total amount of either or both of leucine and phenylalanine, and lysine (the total amount converted to the amount of free form), the total amount of either or both of leucine and phenylalanine, and one or more kinds selected from the group consisting of valine, isoleucine, histidine and tryptophan (the total amount converted to the amount of free form), or the total amount of either or both of leucine and phenylalanine, lysine, and one or more kinds selected from the group consisting of valine, isoleucine, histidine and tryptophan (the total amount converted to the amount of free form).

In addition, the ingestion or dosing period of the composition of the present invention is also appropriately determined according to the condition and symptoms of the application subject, and the like. Considering that a decline in cognitive function occurs along with aging and various diseases, intracerebral lesions such as cerebral atrophy and the like, and the like, and chronically progresses, or that anxiety-like symptoms appear along with a decline in cognitive function, or before and after the decline in cognitive function, and persist for a long time, continuous ingestion or administration for a long period of time is preferable to improve cognitive function or anxiety-like symptoms.

The composition of the present invention can be formulated as a unit package form. In the present specification, the "unit package form" means a form of one or more units with a particular amount (e.g., ingestion amount or dose per one time etc.) as one unit is/are filled in one container or packed in a package. For example, a unit package form with ingestion amount or dose per one time as one unit is referred to as "unit package form for ingestion amount or dose per one time". A container or package used for the unit package form can be appropriately selected according to the form and the like of the composition of the present invention. For example, paper container or bag, plastic container or bag, pouch, aluminum can, steel can, glass bottle, pet bottle, PTP (press through pack) package sheet and the like can be mentioned.

The application subject of the composition of the present invention includes, for example, mammals (e.g., human, monkey, mouse, rat, guinea pig, hamster, rabbit, cat, dog, bovine, horse, donkey, swine, sheep, etc.), birds (e.g., duck, chicken, goose, turkey, etc.) and the like.

When the composition of the present invention is applied to an application subject animal (hereinafter to be also simply referred to as "subject animal") other than human, the ingestion amount or dose of the composition of the present invention can be appropriately set according to the kind, sex, body weight and the like of the subject animal.

The composition of the present invention has a cognitive function improving effect, and is effective for the prophylaxis or improvement of various symptoms or disorders caused by a decline in cognitive function such as a decline in learning ability and memory, learning and memory disorder, and the like.

In addition, the composition of the present invention has an improving effect on anxiety-like symptoms, and is effective for the prophylaxis of the expression of anxiety-like symptoms such as anxiety, agitation and the like or reduction of the aforementioned symptoms.

Particularly, it is effective for preventing the expression of anxiety-like symptoms that appear along with a decline in cognitive function or before and after the decline of cognitive function, or for reducing the aforementioned symptoms.

Furthermore, the composition of the present invention has an effect of suppressing cerebral atrophy, cerebral atrophy observed in neurodegenerative diseases such as Alzheimer-type dementia and the like, cerebral atrophy that appears and progresses along with aging, and the like, and is effective for improving a decline in cognitive function caused by these.

Particularly, since the composition of the present invention contains amino acids, which are contained in foods and have abundant food experience, as active ingredients, it is highly safe, suitable for continuous ingestion or administration, and thus suitable for preventing or improving a decline in cognitive that chronically progresses for a long time along with aging and the like, improving anxiety-like symptoms that persist for a long time, or suppressing the appearance and progression of cerebral atrophy.

Therefore, the composition of the present invention can be preferably ingested by or administered to those exhibiting symptoms or disorders due to a decline in cognitive function, elderly people and middle- or late middle-aged persons requiring improvement of cognitive function, and the like.

In addition, the composition of the present invention can be preferably ingested by or administered to those exhibiting the above-mentioned anxiety-like symptoms, and elderly people and middle- or late middle-aged persons who may develop the above-mentioned anxiety-like symptoms, and the like.

Furthermore, the composition of the present invention can be preferably ingested by or administered to patients with neurodegenerative diseases in which appearance and progression of cerebral atrophy are observed, such as Alzheimer-type dementia and the like, elderly people who are highly likely to show appearance and progression of cerebral atrophy, and the like.

The composition of the present invention can be provided as a pharmaceutical product (hereinafter to be also referred to as "the pharmaceutical product of the present invention" in the present specification) directly or by further adding the above-mentioned pharmaceutically acceptable additives.

The pharmaceutical product of the present invention can have a dosage form of oral preparation such as tablet, coated tablet, chewable tablet, pill, (micro)capsule, granule, fine granule, powder, elixir, lemonade, syrup, suspension, emulsion, oral jelly and the like, injection such as solution, suspension, emulsion and the like, solid injection to be used by dissolving or suspending when in use, injectable preparation such as transfusion, sustainable injection and the like, tubal liquid, and the like.

The pharmaceutical product of the present invention may contain an anti-dementia drug as long as the characteristics of the present invention are not impaired.

Examples of the anti-dementia drug include acetylcholinesterase inhibitors such as donepezil hydrochloride, galanthamine, rivastigmine and the like; and NMDA receptor antagonists such as memantine and the like, and these can be used according to general dosage and administration.

The pharmaceutical product of the present invention can be preferably administered to patients exhibiting symptoms or disorders due to a decline in cognitive function, patients who may develop the aforementioned symptoms or disorders, elderly people and middle- or late middle-aged persons exhibiting a decline in cognitive function, and the like.

In addition, the pharmaceutical product of the present invention can be preferably administered to patients exhibiting anxiety-like symptoms that appear along with a decline in cognitive function or before and after a decline in cognitive function, elderly people and middle- or late middle-aged persons exhibiting the aforementioned anxiety-like symptoms, and the like.

Furthermore, the pharmaceutical product of the present invention can be preferably ingested by or administered to patients with neurodegenerative diseases in which appearance and progression of cerebral atrophy are observed, such as Alzheimer-type dementia and the like, elderly people and middle- or late middle-aged persons who may be affected with the aforementioned neurodegenerative diseases, elderly people who are highly likely to show appearance and progression of cerebral atrophy, and the like.

The pharmaceutical product of the present invention is administered per day to the above-mentioned application subject such that the total amount of one or more kinds selected from the group consisting of leucine and phenylalanine (i.e., either or both of leucine and phenylalanine) (the total amount converted to the amount of free form), the total amount of either or both of leucine and phenylalanine, and lysine (the total amount converted to the amount of free form), the total amount of either or both of leucine and phenylalanine, and one or more kinds selected from the group consisting of valine, isoleucine, histidine and tryptophan (the total amount to converted to the amount of free form), or the total amount of either or both of leucine and phenylalanine, lysine, and one or more kinds selected from the group consisting of valine, isoleucine, histidine and tryptophan (the total amount converted to the amount of free form) would be the above-mentioned daily dose.

Furthermore, the composition of the present invention can be ingested by adding to various foods. The food to which the composition of the present invention is added is not particularly limited, and may be any as long as it is a food in the form generally served for meals or dessert.

For example, the composition of the present invention is added to drinks such as beverage water and the like, and a suitable flavor is added when desired, whereby a drink can be provided.

More specifically, the composition of the present invention can be added, for example, to beverage water such as fruit juice drinks, sport drinks and the like; dairy products such as milk, yogurt and the like; confectionery such as jelly, chocolate, candy, biscuit and the like, and the like.

The composition of the present invention is preferably added to the above-mentioned various foods in the amounts to be ingested per day such that the total amount of one or more kinds selected from the group consisting of leucine and phenylalanine (i.e., either or both of leucine and phenylalanine) (the total amount converted to the amount of free form), the total amount of either or both of leucine and phenylalanine, and lysine (the total amount converted to the amount of free form), the total amount of either or both of leucine and phenylalanine, and one or more kinds selected from the group consisting of valine, isoleucine, histidine and tryptophan (the total amount converted to the amount of free form), or the total amount of either or both of leucine and phenylalanine, lysine, and one or more kinds selected from the group consisting of valine, isoleucine, histidine and tryptophan (the total amount converted to the amount of free form) would be the above-mentioned ingestion amount per day.

The composition of the present invention can be provided as a food (hereinafter to be also referred to as "the food of the present invention" in the present specification) directly or by adding general food additives as necessary and according to a general food production technique.

The food of the present invention can be prepared as various forms such as liquid (e.g., solution, suspension, emulsified liquid and the like); semi-solid (e.g., gel, cream and the like); solid (e.g., powder, granule, sheet, capsule, tablet and the like), and the like.

Furthermore, the food of the present invention can be prepared as various food forms such as beverage water (fruit juice drinks, sport drinks, coffee drinks, tea drinks etc.), dairy product (lactic fermenting beverage, fermented milk, butter, cheese, yogurt, processed milk, defatted milk etc.), meat product (ham, sausage, hamburger etc.), fish meat processed seafood paste product (fish cake, tube-shaped fish sausage, deep-fried ball of fish paste etc.), egg product (rolled Japanese-style egg omelette, steamed egg custard etc.), confectionery (cookie, jelly, chewing gum, candy, snack food, frozen dessert etc.), bread, noodles, pickle, dried fish, food boiled in soy sauce, soup, seasoning and the like by adding the composition of the present invention to various food starting materials and adding general food additives as necessary. It may also be a bottled food, canned food or retort pouch food.

As the above-mentioned food additive, manufacturing agent (brine, binding agent etc.), thickening stabilizer (xanthan gum, sodium carboxymethylcellulose etc.), gelation agent (gelatin, agar, carrageenan etc.), gum base (vinyl acetate resin, jelutong, chicle etc.), emulsifier (glycerol fatty acid ester, sucrose fatty acid ester, saponin, lecithin etc.), preservative (benzoic acid, sodium benzoate, sorbic acid, potassium sorbate, ε-polylysine etc.), antioxidant (ascorbic acid, erythorbic acid, catechin etc.), glazing agent (shellac, paraffin wax, beeswax etc.), fungicide (thiabendazole, fludioxonil etc.), leavening agent (sodium hydrogen carbonate, glucono-δ-lactone, alum etc.), sweetener (aspartame, acesulfame potassium, licorice extract etc.), bittering agent (caffeine, naringin, worm wood extract etc.), acidulant (citric acid, tartaric acid, lactic acid etc.), seasoning (sodium L-glutamate, disodium 5'-inosinate etc.), colorant (annatto dye, turmeric dye, gardenia dye etc.), flavor (synthetic flavor such as ethyl acetoacetate, anisaldehyde and the like, natural flavor such as orange, lavender and the like) and the like can be mentioned.

In the present invention, one or more kinds of the above-mentioned food additives can be used.

The food of the present invention can be preferably ingested by elderly people and middle- or late middle-aged persons showing a decline in cognitive function, elderly people and middle- or late middle-aged persons who may show a decline in cognitive function, and further, a wide range of subjects for the purpose of preventing a decline in cognitive function.

In addition, the food of the present invention can be ingested by elderly people and middle- or late middle-aged persons exhibiting anxiety-like symptoms that appear along with a decline in cognitive function or before and after a decline in cognitive function, elderly people and middle- or late middle-aged persons who may express the aforementioned anxiety-like symptoms, and further, a wide range of subjects for the purpose of preventing expression of the aforementioned anxiety-like symptoms.

Furthermore, the food of the present invention can be widely ingested by patients with neurodegenerative diseases in which appearance and progression of cerebral atrophy are observed, such as Alzheimer-type dementia and the like, elderly people and middle- or late middle-aged persons who may be affected with the aforementioned neurodegenerative diseases, elderly people who are highly likely to show appearance and progression of cerebral atrophy, and the like, for the purpose of suppressing the appearance and progression of cerebral atrophy.

Therefore, the food of the present invention can also be provided as food with health claims such as food for specified health uses, food with nutrient function claims, food with function claims and the like, food for special dietary uses such as food for sick people, food for the elderly and the like, health supplement, and the like for improving cognitive function or anxiety-like symptoms, or for suppressing cerebral atrophy.

The food of the present invention is preferably ingested per day by the above-mentioned application subject such that the total amount of one or more kinds selected from the group consisting of leucine and phenylalanine (i.e., either or both of leucine and phenylalanine) (the total amount converted to the amount of free form), the total amount of either or both of leucine and phenylalanine, and lysine (the total amount converted to the amount of free form), the total amount of either or both of leucine and phenylalanine, and one or more kinds selected from the group consisting of valine, isoleucine, histidine and tryptophan (the total amount converted to the amount of free form), or the total amount of either or both of leucine and phenylalanine, lysine, and one or more kinds selected from the group consisting of valine, isoleucine, histidine and tryptophan (the total amount converted to the amount of free form) would be the above-mentioned ingestion amount per day.

Furthermore, the present invention also provides a method for improving cognitive function in a subject animal in need of improvement of cognitive function (hereinafter to be also referred to as the "method of the present invention" in the present specification).

The method of the present invention includes allowing a subject animal in need of improving cognitive function to ingest a composition containing one or more kinds selected from the group consisting of 25 mol % to 45 mol % of leucine, and 20 mol % to 40 mol % of phenylalanine relative to the total content of seven amino acids, in an amount effective for improving cognitive function of the subject animal, or administering said amount of the composition to the animal.

In the method of the present invention, ingestion or administration of a composition containing both leucine and phenylalanine at the above-mentioned composition ratio is preferable, ingestion or administration of a composition further containing 10 mol % to 30 mol % of lysine relative to the total content of seven amino acids in addition to one or more kinds selected from the group consisting of leucine and phenylalanine at the above-mentioned composition ratio is more preferable, and ingestion or administration of a composition containing leucine, phenylalanine and lysine at the above-mentioned composition ratio is further preferable.

In the method of the present invention, ingestion or administration of a composition further containing one or more kinds selected from the group consisting of valine, isoleucine, histidine and tryptophan in addition to one or more kinds selected from the group consisting of leucine and phenylalanine at the above-mentioned composition ratio, or one or more kinds selected from the group consisting of leucine and phenylalanine, and lysine at the above-mentioned composition ratio is preferable.

From the aspect of a cognitive function improving effect, in the method of the present invention, ingestion or administration of a composition containing leucine, phenylalanine and lysine at the above-mentioned composition ratio, and one or more kinds selected from the group consisting of valine, isoleucine, histidine and tryptophan is more preferable, and ingestion or administration of a composition containing leucine, phenylalanine and lysine at the above-mentioned composition ratio, and valine, isoleucine, histidine and tryptophan is particularly preferable.

In the method of the present invention, the content of valine in the composition to be ingested by or administered to a subject animal is preferably 2 mol % to 7 mol %, more preferably 4 mol % to 6 mol %, relative to the total content of seven amino acids.

The content of isoleucine in the composition to be ingested by or administered to a subject animal is preferably 5 mol % to 15 mol %, more preferably 7 mol % to 13 mol %, relative to the total content of seven amino acids.

The content of histidine in the composition to be ingested by or administered to a subject animal is preferably 2 mol % to 10 mol %, more preferably 2.5 mol % to 8 mol %, relative to the total content of seven amino acids.

The content of tryptophan in the composition to be ingested by or administered to a subject animal is preferably 0.1 mol % to 2 mol %, more preferably 0.3 mol % to 1 mol %, relative to the total content of seven amino acids.

The subject animal in the method of the present invention includes mammal (e.g., human, monkey, mouse, rat, guinea pig, hamster, rabbit, cat, dog, bovine, horse, donkey, swine, sheep etc.), birds (e.g., duck, chicken, goose, turkey etc.) and the like.

The method of the present invention is effective for the prophylaxis or improvement of various symptoms or disorders caused by a decline in cognitive function such as a decline in learning ability and memory, learning and memory disorder, and the like.

In addition, the method of the present invention is effective for improving anxiety-like symptoms, namely, for the prophylaxis of the expression of anxiety-like symptoms such as anxiety, agitation and the like or reduction of the aforementioned anxiety-like symptoms. It is particularly effective for preventing the expression of anxiety-like symptoms that appear along with a decline in cognitive function or before and after the decline of cognitive function, or for reducing the aforementioned anxiety-like symptoms.

Furthermore, the method of the present invention is effective for suppressing cerebral atrophy observed in neurodegenerative diseases such as Alzheimer-type dementia and the like, cerebral atrophy that appears and progresses along with aging, and the like, and thus effective for improving a decline in cognitive function caused by these.

Particularly, since the method of the present invention uses amino acids, which are contained in foods and have abundant food experience, as an active ingredient, it has high safety and can be applied continuously.

In the case of human, the method of the present invention is preferably applied to patients exhibiting symptoms and disorders due to a decline in cognitive function, and elderly people, and middle- or late middle-aged persons requiring prevention of a decline in cognitive function such as elderly people, and middle- or late middle-aged persons who may show a decline in cognitive function.

In addition, the method of the present invention is preferably applied to elderly people and middle- or late middle-aged persons exhibiting anxiety-like symptoms, and elderly people and middle- or late middle-aged persons who may express anxiety-like symptoms, and particularly preferably applied to elderly people and middle- or late middle-aged persons exhibiting anxiety-like symptoms that appear along with a decline in cognitive function or before and after a decline in cognitive function, and elderly people and middle- or late middle-aged persons who may express the aforementioned anxiety-like symptoms.

Furthermore, the method of the present invention is preferably applied to patients with neurodegenerative disease who are known to show cerebral atrophy such as Alzheimer-type dementia and the like, elderly people and middle- or late middle-aged persons who may be affected with the aforementioned neurodegenerative diseases, elderly people who may show cerebral atrophy, and the like.

The effective amount of the composition containing one or more kinds selected from the group consisting of leucine and phenylalanine at the above-mentioned composition ratio in the method of the present invention is appropriately determined according to the kind, age, sex, the condition or level of a decline in cognitive function, intracerebral lesion or anxiety-like symptoms and the like of the subject animal. An amount similar to the above-mentioned ingestion amount or dose of the composition of the present invention for a human or a subject animal other than human can be ingested or administered at the frequency and period mentioned above.

As an ingestion or administration method of the composition containing one or more kinds selected from the group consisting of leucine and phenylalanine at the above-mentioned composition ratio and the like in the method of the present invention, oral ingestion or oral administration, enteral tube administration, administration by infusion and the like can be mentioned. Oral ingestion or oral administration is preferable since convenient ingestion is possible without the need to perform under the guidance and supervision of a doctor at a medical institution.

Other features of the invention will become apparent in the course of the following descriptions of exemplary embodiments which are given for illustration of the invention and are not intended to be limiting thereof.

EXAMPLES

Example 1

Composition for Improving Cognitive Function

To afford the composition shown in Table 1, given amounts of respective components were weighed and mixed to prepare the composition for improving cognitive function of Example 1 (hereinafter to be referred to as "the composition of Example 1"). Similarly, a composition with the composition ratio shown in Table 1 was prepared and used as Comparative Example 1.

TABLE 1

| component | composition ratio relative to total content of amino acids (mol %) | |
|---|---|---|
| | Example 1 | Comparative Example 1 |
| L-leucine | 36.10 | 20.32 |
| L-lysine hydrochloride | 18.42 | 20.54 |
| L-valine | 5.02 | 4.06 |
| L-isoleucine | 9.96 | 3.63 |
| L-phenylalanine | 26.09 | 17.72 |
| L-histidine hydrochloride | 3.89 | 33.13 |
| L-tryptophan | 0.52 | 0.60 |
| total amount | 100 | 100 |

Experimental Example 1. Study of Effect on Learning and Memory Functions

Using C57Bl/6j aged mice (58-week-old to 61-week-old, male) (purchased from CHARLES RIVER LABORATORIES JAPAN, INC.), an effect of the compositions of Example 1 and Comparative Example 1 on learning and memory functions was studied.

C57Bl/6j aged mice were divided into 4 groups as shown in Table 2 (n=12/group). To a group allowed to freely ingest a normal protein diet (containing 20 wt % casein) was administered a vehicle alone (NPD+Veh.). The other 3 groups were allowed to freely ingest a low-protein diet (containing 5 wt % casein), and respectively used as a group administered with a vehicle alone (LPD+Veh.), a group administered with the composition of Example 1 (LPD+E1), and a group administered with the composition of Comparative Example 1 (LPD+C1). In LPD+E1 and LPD+C1, the composition of Example 1 (E1) and the composition of Comparative Example 1 (C1) at 1 g/kg body weight were each dissolved in 0.5 wt % methylcellulose aqueous solution, and continuously administered by oral gavage (cycle of 2 days off after administration for 5 consecutive days) 2 times daily (morning and evening) for 2 months. A 0.5 wt % methylcellulose aqueous solution (Vehicle) was similarly administered to NPD+Veh. and LPD+Veh.

TABLE 2

| group | diet | administered sample |
|---|---|---|
| NPD + Veh. | diet containing 20 wt % casein | vehicle (0.5 wt % methylcellulose aqueous solution) |
| LPD + Veh. | diet containing 5 wt % casein | vehicle (0.5 wt % methylcellulose aqueous solution) |
| LPD + C1 | diet containing 5 wt % casein | sample containing the composition of Comparative Example 1 |
| LPD + E1 | diet containing 5 wt % casein | sample containing the composition of Example 1 |

The mice of each group shown in Table 2 were subjected to a passive avoidance test as follows after 1-month administration and 2-month administration of a vehicle or each composition of Example 1 and Comparative Example 1.

(i) Using an apparatus composed of light/dark compartments with an electrical stimulation device in the dark compartment, mice were placed in the light compartment. When the mice entered the dark compartment, the door was closed simultaneously with the entry, and an electrical stimulation (1 mA, 1 sec) was applied. The entry into the dark compartment was defined to be the time point when the base of the tail entered the dark compartment.

(ii) (i) was tried once, and 24 hr later, the mice were placed in a light compartment, and the time until the mice entered a dark compartment (transfer latency time) was measured. In addition, the proportion of individuals that stayed in the light compartment for a maximum evaluation time of 480 seconds, that is, the proportion of individuals that memorized that the dark compartment is scary by one electrical stimulation (achievement by 1st ES) was determined.

A vehicle or the composition of Example 1 or Comparative Example 1 was administered for one month, then a passive avoidance test was performed, and the time required by the mice in each group until they enter the dark compartment (transfer latency time) was measured. The results are shown in FIG. 1 as mean+standard error of the mean of each of 12 mice.

In addition, the proportion of individuals that memorized that the dark compartment is scary by one electrical stimulation (achievement by 1st ES) is also shown in FIG. 1. The numerical values in the Figure show the number of mice in each group that remained in the light compartment for 300 sec, after 24 hr from the first trial.

As for the time required for the entry into a dark compartment (transfer latency time), which was measured 24 hr after the first trial, one-way analysis of variance and Dunnett's multiple comparison test were performed with respect to the group raised on a normal protein diet and administered with a vehicle alone (NPD+Veh.). As for the proportion of individuals that memorized that the dark compartment is scary by one electrical stimulation (achievement by 1st ES), a chi-square test was performed with respect to NPD+Veh.

As shown in FIG. 1, the time required for the entry into a dark compartment (transfer latency time) 24 hr after the first trial, drastically decreased in the group raised on a low-protein diet and administered with a vehicle alone (LPD+Veh.) as compared to the group raised on a normal protein diet and administered with a vehicle alone (NPD+Veh.) ($p<0.05$).

In the group orally administered with the composition of Example 1 of the present invention in addition to a low-protein diet (LPD+E1), it was observed that the transfer latency time was recovered to such an extent that no significant difference was observed between LPD+E1 and NPD+Veh.

On the other hand, the group that received oral administration of the composition of Comparative Example 1 in addition to a low-protein diet (LPD+C1), the transfer latency time was not recovered.

The proportion of individuals that memorized that the dark compartment is scary by one electrical stimulation (achievement by 1st ES) decreased in LPD+Veh. as compared to NPD+Veh., and was recovered in LPD+E1 to the same level as NPD+Veh. LPD+C1 did not show such recovery.

Experimental Example 2. Study of Effect on Learning and Memory Functions (Reproducibility Test)

Using C57Bl/6j mature mice (19-week-old, male) (purchased from CHARLES RIVER LABORATORIES JAPAN, INC.), the effect of the composition of Example 1 on the learning and memory functions was studied.

Figure 2:
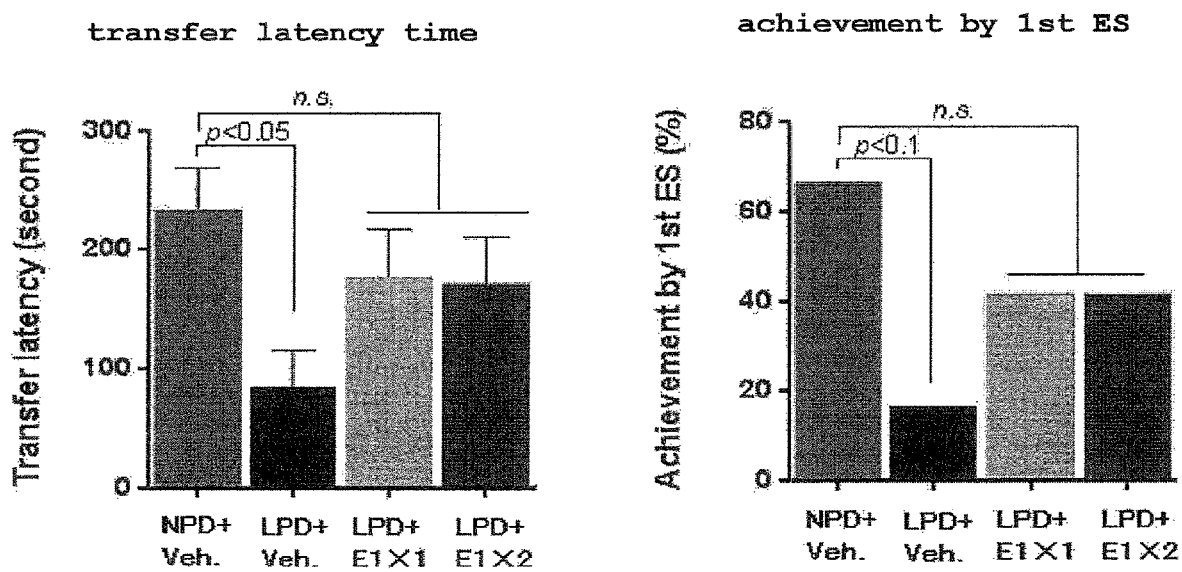
FIG. 2 shows the effects of the composition of Example 1 of the present invention on transfer latency time and achievement by 1st ES in the passive avoidance test (reproducibility test) in Experimental Example 2. In the Figure, "n.s." indicates no significant difference at critical rate (p)=5%.

C57Bl/6j mature mice were divided into 4 groups (n=12/group) shown in Table 3. To a group raised on a normal protein diet and administered with a vehicle alone (NPD+Veh.), a group raised on a low-protein diet and administered with a vehicle alone (LPD+Veh.), a group raised on a low-protein diet and administered with the composition of Example 1 once per day (1 g/kg body weight per administration) (LPD+E1×1), and a group raised on a low-protein diet and administered with the composition of Example 1 twice per day (1 g/kg body weight per administration) (LPD+E1×2) was administered a vehicle or the composition of Example 1 for 1 to 1.5 months, and a passive avoidance test was performed in the same manner as in Experimental Example 1, and the time required until entry into the dark compartment (transfer latency time) 24 hr after the first trial, and the proportion of individuals that memorized that the dark compartment is scary by one electrical stimulation (achievement by 1st ES) were determined. The transfer latency time and achievement by 1st ES in the passive avoidance test performed after administration for one month are shown in FIG. 2 as mean+standard error of the mean of each of 12 mice. As for the transfer latency time, one-way analysis of variance and Dunnett's multiple comparison test were performed with respect to the group raised on a normal protein diet and administered with a vehicle alone (NPD+Veh.). As for the achievement by 1st ES, a chi-square test was performed with respect to NPD+Veh.

TABLE 3

| group | diet | administered sample |
|---|---|---|
| NPD + Veh. | diet containing 20 wt % casein | vehicle (0.5 wt % methylcellulose aqueous solution) |
| LPD + Veh. | diet containing 5 wt % casein | vehicle (0.5 wt % methylcellulose aqueous solution) |
| LPD + E1 × 1 | diet containing 5 wt % casein | sample containing the composition of Example 1, administered once per day |
| LPD + E1 × 2 | diet containing 5 wt % casein | sample containing the composition of Example 1, administered twice per day |

As shown in FIG. 2, the transfer latency time and the achievement by 1st ES showed a significant ($p<0.05$ and $p<0.1$) decrease also in mature mice in the group raised on a low-protein diet and administered with a vehicle alone (LPD+Veh.) as compared to the group raised on a normal protein diet and administered with a vehicle alone (NPD+Veh.). In the group raised on a low-protein diet and administered with the composition of Example 1 (LPD+E1×1 and LPD+E1×2), it was found that both the transfer latency time and the achievement by 1st ES that decreased by raising on a low-protein diet were recovered to such an extent that no significant difference was observed from when raised on a normal protein diet.

The sample containing the composition of Example 1 of the present invention, even when administered once per day, showed the same level of effect as that achieved when administered twice per day.

From the results of the above-mentioned Experimental Examples 1 and 2, it was suggested that the composition of Example 1 of the present invention suppresses and improves a decrease in the learning and memory functions caused by the ingestion of a low-protein diet.

Experimental Example 3. Study of Effect on Anxiety, Agitation and Hyperactivity Symptoms Using C57Bl/6j aged mice (58-week-old to 61-week-old, male) (purchased from CHARLES RIVER LABORATORIES JAPAN, INC.), an effect of the compositions of Example 1 of the present invention and the composition of Comparative Example 1 on anxiety, agitation and hyperactivity symptoms was evaluated by an elevated plus maze test.

C57Bl/6j aged mice were grouped as shown in Table 2 (n=12/group), and each group was subjected to an elevated plus maze test as follows after 1-month administration and 2-month administration of a vehicle or each composition of Example 1 and Comparative Example 1.

Figure 3:
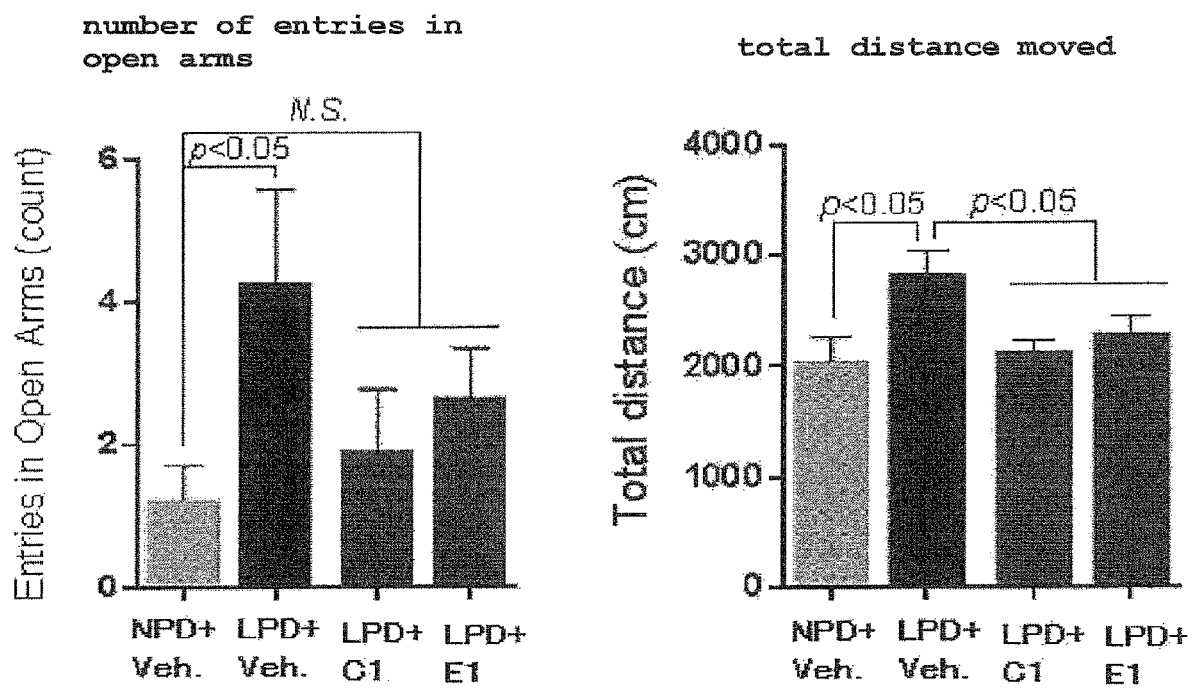
FIG. 3 shows the effects of the composition of Example 1 of the present invention on the number of entries in open arms, which is an index of anxiety and agitation symptoms, and the total distance moved, which is an index of hyperactivity, in the elevated plus maze test in Experimental Example 3. In the Figure, "N.S." indicates no significant difference at critical rate (p)=5%.

That is, the mice in each group were placed in the neutral zone of the elevated plus maze, and the behavior of the mice was observed for 8 min. The number of times the mouse entered the runway without a wall (open arm) and the distance moved within the track were analyzed using video tracking behavior analysis software Smart3.0 (Panlab), and the number of entries in open arms (rate of entries in open arms) and the total distance moved were calculated. The rate of entries in open arms becomes an index of anxiety and agitation symptoms, and the total distance moved becomes an index of hyperactivity symptoms. The rate of entries in open arms after 2 months of administration and the total distance moved after 1 month of administration are shown in FIG. 3 as mean+standard error of the mean. As for the number of entries in open arms, one-way analysis of variance and Dunnett's multiple comparison test were performed between the group raised on a normal protein diet and administered with a vehicle alone (NPD+Veh.) and other groups. As for the total distance moved, one-way analysis of variance and Dunnett's multiple comparison test were performed between NPD+Veh. and the group raised on a low-protein diet and administered with a vehicle alone (LPD+Veh.), between LPD+Veh. and each of the group raised on a low-protein diet and administered with the composition of Example 1 of the present invention (LPD+E1), and the group raised on a low-protein diet and administered with the composition of Comparative Example 1 (LPD+C1).

As shown in FIG. 3, both the number of entries in open arms, and the total distance moved showed a significant ($p<0.05$) increase in the group raised on a low-protein diet and administered with a vehicle alone (LPD+Veh.) as compared to the group raised on a normal protein diet and administered with a vehicle alone (NPD+Veh.).

On the other hand, in the group raised on a low-protein diet and administered with the composition of Example 1 of the present invention (LPD+E1), the number of entries in open arms showed an increase of a level without a significant difference from that of NPD+Veh., and the total distance moved significantly decreased ($p<0.05$) as compared to LPD+Veh.

The same results as in LPD+E1 were also obtained in the group raised on a low-protein diet and administered with the composition of Comparative Example 1 (LPD+C1).

Experimental Example 4. Study of Effect on Anxiety, Agitation and Hyperactivity Symptoms (Reproducibility Test)

Using C57Bl/6j mature mice (19-week-old, male) (purchased from CHARLES RIVER LABORATORIES JAPAN, INC.), the effect of the composition of Example 1 on agitation, anxiety and hyperactivity symptoms was evaluated by an elevated plus maze test.

C57Bl/6j mature mice were grouped (n=12/group) as shown in Table 3. After 1-month to 1.5-month administration of the composition of Example 1 and a vehicle, the mice in each group were placed in the neutral zone of the elevated plus maze, and the behavior of the mice was observed for 8 min. Similar to the case of Experimental Example 3, the number of entries in open arms and the total distance moved were determined, and the evaluation results of the number of entries in open arms after 1-month administration are shown in FIG. 4 as mean+standard error of the mean.

As for the total distance moved, the group raised on a normal protein diet and administered with a vehicle alone (NPD+Veh.) showed the same level of increase as the group raised on a low-protein diet and administered with a vehicle alone (LPD+Veh.), and the effect of the composition of Example 1 could not be evaluated.

Figure 4:
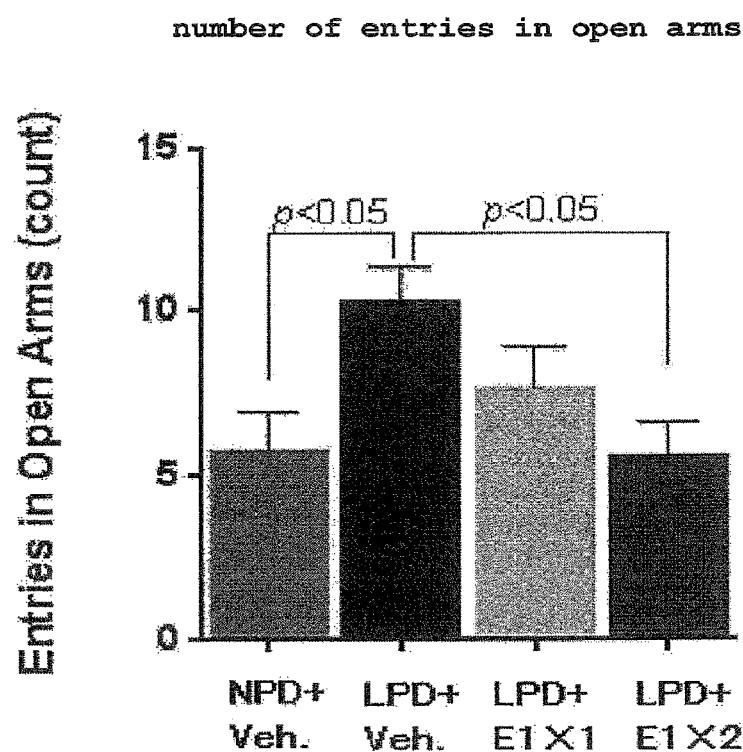
FIG. 4 shows the effects of the composition of Example 1 of the present invention on the number of entries in open arms, which is an index of anxiety and agitation symptoms, in the elevated plus maze test (reproducibility test) in Experimental Example 4.

As for the results shown in FIG. 4, one-way analysis of variance and Dunnett's multiple comparison test were performed between NPD+Veh. and LPD+Veh., between LPD+Veh. and each of the groups raised on a low-protein diet and administered with the composition of Example 1 once per day (1 g/kg body weight per administration) (LPD+E1×1), and the group raised on a low-protein diet and administered with the composition of Example 1 twice per day (1 g/kg body weight per administration) (LPD+E1×2).

As shown in FIG. 4, the number of entries in open arms to be the index of anxiety and agitation significantly ($p<0.05$) increased in LPD+Veh. as compared to NPD+Veh.

On the other hand, a decrease in the number of entries in open arms was found in the group raised on a low-protein diet and administered with the composition of Example 1 once per day (LPD+E1×1), and the number of entries in open arms significantly ($p<0.05$) decreased in the group raised on a low-protein diet and administered with the composition of Example 1 twice per day (LPD+E1×2). That is, it was shown that the decrease in the number of entries in open arms due to the administration of the composition of Example 1 depends on the dose of the composition of Example 1.

The results of Experimental Example 3 suggest that the composition of Example 1 of the present invention suppresses anxiety and agitation symptoms and hyperactivity, and the results of Experimental Example 4 suggest that the composition of Example 1 of the present invention suppresses anxiety and agitation symptoms in a dose-dependent manner.

Experimental Example 5. Study of Effect on Intracerebral Neurotransmitter Concentration In Experimental Example 1 and Experimental Example 3, respective evaluations were performed by a passive avoidance test and an elevated plus maze test, after which the mice in each group were dissected, and the concentration of the neurotransmitters (dopamine, norepinephrine, glutamic acid) in the prefrontal cortex was measured using the high performance liquid chromatograph (HPLC) method and the liquid chromatography mass spectrometry (LC/MS) method. As for the measurement results of the concentrations of dopamine and glutamic acid, one-way analysis of variance and Tukey's multiple comparison test were performed between the group raised on a normal protein diet and administered with a vehicle alone (NPD+Veh.) and the group raised on a low-protein diet and administered with a vehicle alone (LPD+Veh.), between LPD+Veh. and each of the group raised on a low-protein diet and administered with the composition of Example 1 (LPD+E1), and the group raised on a low-protein diet and administered with the composition of Comparative Example 1 (LPD+C1), and as for the measurement results of the norepinephrine concentration, between NPD+Veh. and LPD+Veh., and between NPD+Veh. and each group of LPD+E1 and LPD+C1. The results are shown in FIG. 5 as mean+standard error of the mean.

Figure 5:
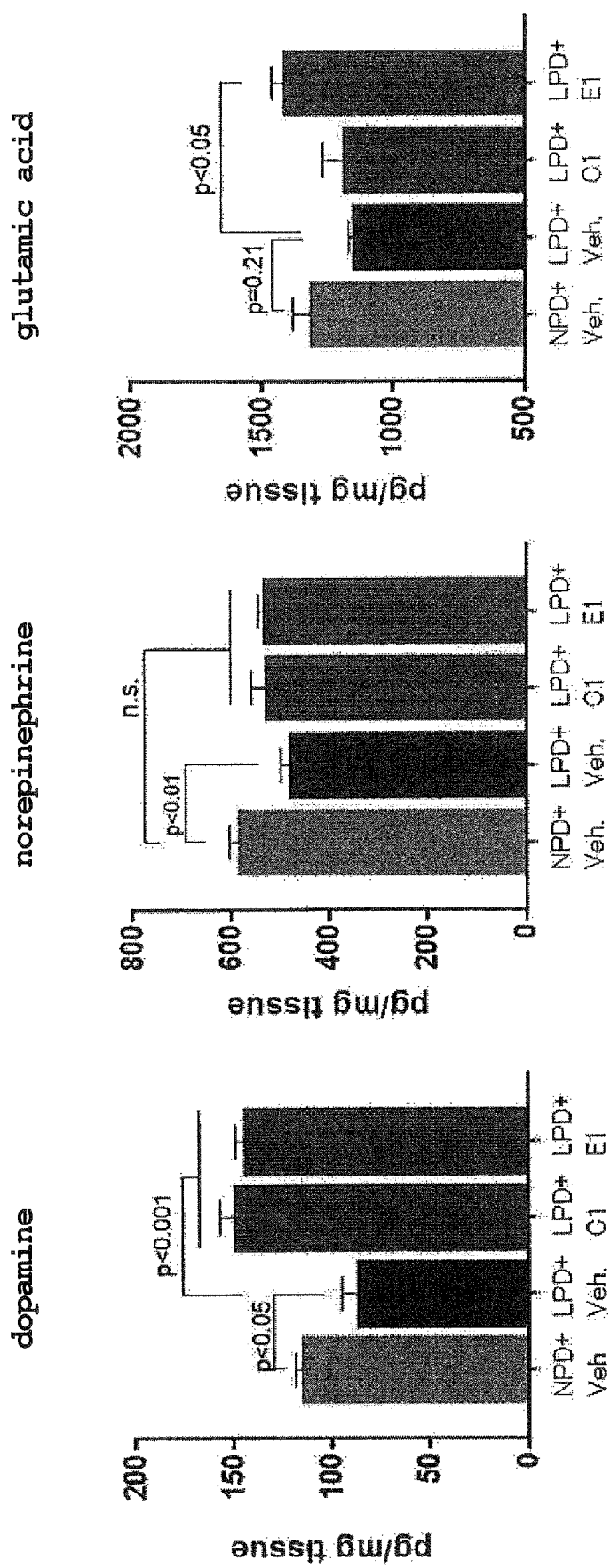
FIG. 5 shows the effects of the composition of Example 1 of the present invention on the intracerebral neurotransmitter concentration in Experimental Example 5. In the Figure, "n.s." indicates no significant difference at critical rate (p)=5%.

As shown in FIG. 5, it was found that the concentration of each of intracerebral dopamine, norepinephrine and glutamic acid decreased in the group raised on a low-protein diet and administered with a vehicle alone (LPD+Veh.) as compared to the group raised on a normal protein diet and administered with a vehicle alone (NPD+Veh.) (significant at $p<0.05$, significant at $p<0.01$, and significant tendency at $p=0.21$, respectively).

On the other hand, a significant increase in the intracerebral dopamine concentration and glutamic acid concentration was found (significant at $p<0.001$ and $p<0.05$, respectively) in the group raised on a low-protein diet and administered with the composition of Example 1 (LPD+E1) as compared to the LPD+Veh. group, and it was found that the intracerebral norepinephrine concentration increased to a level without significant difference from the NPD+Veh. group.

Dopamine, norepinephrine and glutamic acid that decreased in the group raised on a low-protein diet in Experimental Example 5 are intracerebral neurotransmitters known to decrease in dementia patients.

From the results of Experimental Example 5, it was suggested that the composition of the present invention may improve a decrease in the intracerebral neurotransmitters and improve cognitive function.

Experimental Example 6. Study of Influence on Brain-Derived Neurotrophic Factor (BDNF) Gene Expression Brain-derived neurotrophic factor (BDNF) is one of the proteins belonging to the neurotrophic factor family and has various functions in the cranial nervous system, such as survival of nerve cells, formation of neural network, and expression of higher brain functions such as memory consolidation and the like. In addition, a decrease in BDNF expression level is observed in various neurodegenerative diseases including dementia and psychiatric diseases, and a drug that induces the expression of BDNF or a composition containing the same is expected to show an effect of improving brain function impaired by neurodegenerative diseases or psychiatric diseases.

Thus, an influence of the above-mentioned composition of Example 1 of the present invention on the expression of BDNF gene was studied.

In the above-mentioned Experimental Example 1 and Experimental Example 3, respective evaluations were performed by a passive avoidance test and an elevated plus maze test, after which the mice in each group were dissected to obtain cerebral cortex tissue, and the expression level of the BDNF gene in the cerebral cortex tissue was studied by measuring changes in the mRNA expression level by the RT-qPCR method.

After the completion of respective evaluations in Experimental Example 1 and Experimental Example 3, RNA was extracted using an RNA extraction kit ("RNeasy Mini Kit" (QUIAGEN)) from the cerebral cortex tissue of the mice (n=6/group) of each group shown in Table 4, and a reverse transcription reaction was performed using a reverse transcription reaction premix reagent ("Prime Script (trade mark) RT Master Mix" (Takara Bio Inc.)). Then, changes in the BDNF mRNA expression level of the obtained DNA product were analyzed using a real-time PCR kit ("SYBR (registered trade mark) Select Master Mix" (Applied Biosystems)).

Figure 6:
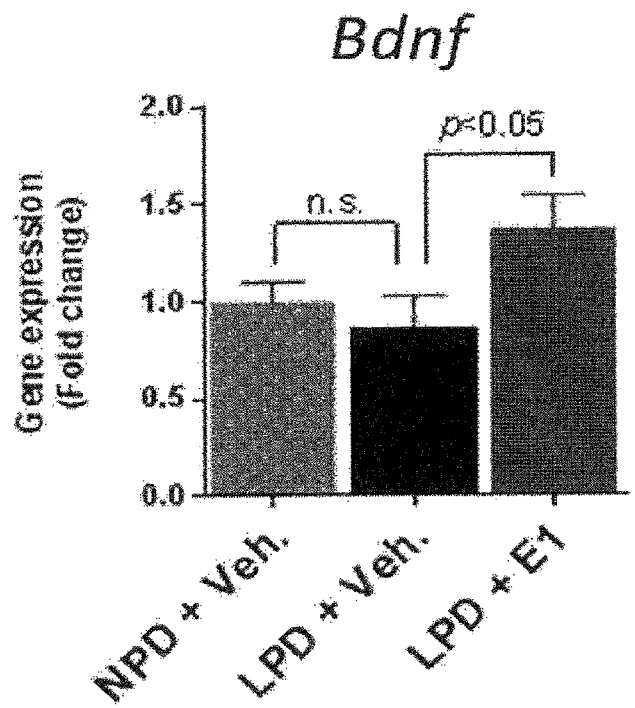
FIG. 6 shows the effects of the composition of Example 1 of the present invention on the expression of brain-derived neurotrophic factor (BDNF) gene in Experimental Example 6. In the Figure, "n.s." indicates no significant difference at critical rate (p)=0.05.

As for the measurement results, the BDNF expression level was compared between the group raised on a normal protein diet and administered with a vehicle alone (NPD+ Veh.) and the group raised on a low-protein diet and administered with a vehicle alone (LPD+Veh.), and the group raised on a low-protein diet and administered with the composition of Example 1 (LPD+E1), and the ratio to NPD+Veh. was determined and shown in FIG. 6 as mean+ standard error of the mean of 6 mice in each group. Statistical analysis of comparison among 3 groups was performed by one-way analysis of variance and Dunnett's multiple comparison test.

TABLE 4

| group | diet | administered sample |
|---|---|---|
| NPD + Veh. | diet containing 20 wt % casein | vehicle (0.5 wt % methylcellulose aqueous solution) (twice per day) |

TABLE 4-continued

| group | diet | administered sample |
|---|---|---|
| LPD + Veh. | diet containing 5 wt % casein | vehicle (0.5 wt % methylcellulose aqueous solution) (twice per day) |
| LPD + E1 | diet containing 5 wt % casein | solution of the composition of Example 1 in 0.5 wt % methylcellulose aqueous solution (1 g/Kg body weight per administration, twice per day) |

As shown in FIG. 6, the expression level of the BDNF gene was significantly (p<0.05) high in the group raised on a low-protein diet and administered with the composition of Example 1 (LPD+E1), as compared to the group raised on a low-protein diet and administered with a vehicle alone (LPD+Veh.).

The above-mentioned results of Experimental Example 6 suggest that the composition of Example 1 of the present invention may induce BDNF gene expression and improve lowered cognitive function.

Experimental Example 7. Study of Influence on Cerebral Atrophy in Alzheimer-Type Dementia Model Mouse In many patients with neurodegenerative diseases including Alzheimer-type dementia, aggregates of fibrotic tau protein are observed in nerve cells and glial cells. rTg4510 transgenic mouse is a mouse transformed to specifically express such tau protein in nerve cells, and is known to exhibit cerebral atrophy with aging. Thus, it is used as a model mouse for Alzheimer-type dementia.

Accordingly, an influence of the composition of Example 1 on cerebral atrophy was studied using rTg4510 mouse and its littermate control mouse.

The 3-month-old male rTg4510 mice and littermate control mice were divided into 3 groups (n=3-4/group) as shown in Table 5, and raised allowing free ingestion of a normal protein diet (containing 20 wt % casein). To one of groups of rTg4510 mice was administered by oral gavage the composition of Example 1 dissolved in 0.5 wt % methylcellulose aqueous solution twice per day (1 g/kg body weight per administration) (rTg4510+E1), and a vehicle (0.5 wt % methylcellulose aqueous solution) alone was administered to the other group of rTg4510 mice and the littermate control mice group (rTg4510+Veh. and Ctrl+Veh.).

At the start of the test and after administration of the vehicle or the composition of Example 1 for 3.5 months, brain magnetic resonance imaging data of each mouse was obtained using 7.0 Tesla MRI for small animals (Bruker), and the volume of cerebral cortex was calculated using image analysis software "Pmod 3.7" (Pmod Technologies Ltd.). The amount of change in the cerebral cortex volume after administration of the vehicle or the composition of Example 1 for 3.5 months relative to the cerebral cortex volume at the start of the test (3-month-old) was determined in each group, and shown in FIG. 7 as mean±standard error of the mean of 3 to 4 mice. Statistical analysis was performed by one-way analysis of variance and Tukey's multiple comparison test of the comparison among 3 groups.

TABLE 5

| group | diet | administered sample |
|---|---|---|
| Ctrl + Veh. | diet containing 20 wt % casein | vehicle (0.5 wt % methylcellulose aqueous solution) (twice per day) |

TABLE 5-continued

| group | diet | administered sample |
|---|---|---|
| rTg4510 + Veh. | diet containing 20 wt % casein | vehicle (0.5 wt % methylcellulose aqueous solution) (twice per day) |
| rTg4510 + E1 | diet containing 20 wt % casein | solution of the composition of Example 1 in 0.5 wt % methylcellulose aqueous solution (1 g/Kg body weight per administration, twice per day) |

Figure 7:
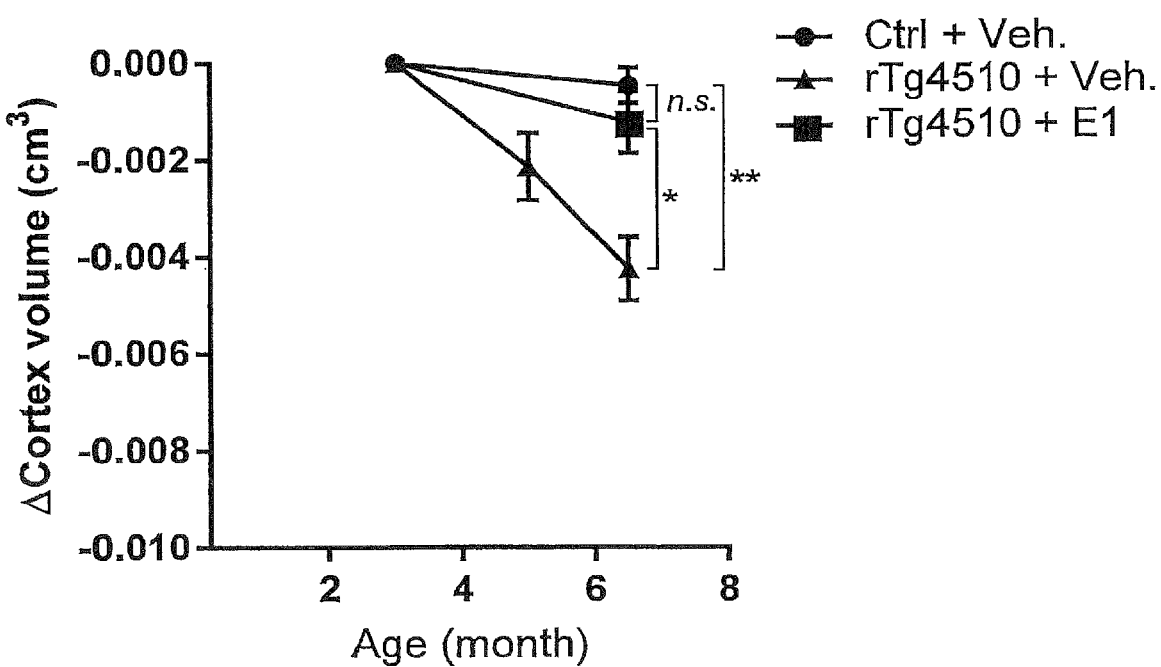
FIG. 7 shows the effects of the composition of Example 1 of the present invention on the volume of cerebral cortex in Experimental Example 7. In the Figure, "n.s." indicates no significant difference at critical rate (p)=0.05, "*" indicates presence of significant difference at p<0.05, and "**" indicates presence of significant difference at p<0.01.

As shown in FIG. 7, a significant (p<0.01) decrease in the cerebral cortex volume was found in the rTg4510 mouse group administered with a vehicle alone (rTg4510+Veh.) as compared to the littermate control mouse group administered with a vehicle alone (Ctrl+Veh.).

On the other hand, the rTg4510 mouse group administered with the composition of Example 1 (rTg4510+E1) showed significant (p<0.05) improvement of a decrease in the cerebral cortex volume as compared to the rTg4510 mouse group administered with a vehicle alone (rTg4510+Veh.), and did not show a significant difference in the cerebral cortex volume as compared to the littermate control mouse group administered with a vehicle alone (Ctrl+Veh.).

The above-mentioned results of Experimental Example 7 suggest that the composition of Example 1 of the present invention may suppress cerebral atrophy observed in Alzheimer-type dementia patients and the like.

Example 2

Composition for Improving Cognitive Function

To afford the composition shown in Table 6, given amounts of respective components were weighed and mixed to prepare a composition for improving cognitive function of Example 2 (hereinafter sometimes to be referred to as "the composition of Example 2").

TABLE 6

| component | composition ratio relative to total content of amino acids (mol %) |
|---|---|
| L-leucine | 36.05 |
| L-lysine hydrochloride | 18.43 |
| L-valine | 5.06 |
| L-isoleucine | 9.97 |
| L-phenylalanine | 26.05 |
| L-histidine hydrochloride | 3.92 |
| L-tryptophan | 0.52 |
| total amount | 100 |

Experimental Example 8. Study of Effect of Composition of Example 2 on Cognitive Function in Human A human clinical test was performed as follows to examine the effect of the composition of Example 2 on cognitive function in humans.

(1) Preparation of Test Food

As shown in Table 7, granules containing the composition of Example 2 (3.0 g) (Active 1), granules containing the composition of Example 2 (1.5 g) (Active 2), and the aforementioned granules containing dextrin, cornstarch, and lactose instead of the composition of Example 2 and not containing either amino acid or protein (Placebo 1) were prepared according to a conventional method.

TABLE 7

| test food | total amount (g) | component |
|---|---|---|
| Active 1 | 4.0 | composition of Example 2 (3.0 g) + excipient (1.0 g) |
| Active 2 | 4.0 | composition of Example 2 (1.5 g) + excipient (2.5 g) |
| Placebo 1 | 4.0 | containing dextrin, cornstarch and lactose instead of composition of Example 2 and not containing either amino acid or protein |

(2) Test Subject

The test subjects were 105 men and women at the age of 55 years or higher (54 males, 51 females, average age=64.3±5.0 years old) with normal cognitive function, that is, no pathological abnormality such as dementia was observed, but the cognitive function test by the Japanese version of the Mini Mental State Examination (MMSE-J) was 26 points or more, and the test by the Japanese version of the Montreal Cognitive Assessment (MoCA-J) was less than 30 points, and they were aware of forgetfulness, or pointed out to be forgetful by others.

(3) Clinical Test

The subjects were randomly divided into 3 groups (test food medium-dose group that ingests Active 1, test food low-dose group that ingests Active 2, and control food group that ingests Placebo 1), cognitive function test (Trail Making Test B (TMT-B)) was performed before ingestion of each test food, and the time to complete the task was measured and used as the baseline value. Thereafter, the test foods shown in Table 7 were ingested when the subjects were hungry (2 packets a day, one packet in the morning and one packet in the afternoon) under double blind test. TMT-B was performed in the same manner 12 weeks after the ingestion, and the time to complete the task was measured.

In the test subjects in each group of the above-mentioned clinical test, no significant difference was found among the 3 groups in sex, age, years of schooling, and the score of the Japanese version of the WHO-5 Well-Being Index (WHO-5-J) and each score of the Tokyo Metropolitan Institute of Gerontology Index of Competence, which relate to cognitive function, as shown in Table 8.

TABLE 8

| | medium-dose group n = 33 | low-dose group n = 35 | control group n = 35 | P |
|---|---|---|---|---|
| sex; proportion of male (males) | 16 (48.5) | 18 (51.4) | 18 (51.4) | n.s. |
| age (years old) | 64.1 (5.9) | 64.1 (5.0) | 64.5 (4.2) | n.s. |
| years of schooling (years) | 14.6 (2.4) | 15.1 (1.8) | 14.7 (2.2) | n.s. |
| score in WHO-5 Well-Being Index (points) | 13.0 (4.0) | 13.3 (3.9) | 12.7 (3.0) | n.s. |
| Tokyo Metropolitan Institute of Gerontology Index of Competence | | | | |
| score of instrumental ADL (points) | 5.0 (0.0) | 5.0 (0.0) | 5.0 (0.0) | n.s. |

TABLE 8-continued

|  | medium-dose group n = 33 | low-dose group n = 35 | control group n = 35 | P |
|---|---|---|---|---|
| score of intellectual ADL (points) | 3.8 (0.5) | 3.7 (0.6) | 3.5 (0.7) | n.s. |
| score of social ADL (points) | 3.7 (0.5) | 3.3 (1.0) | 3.4 (0.9) | n.s. |

*; Numerical values in parentheses show standard deviation values.

(4) Results

Figure 8:
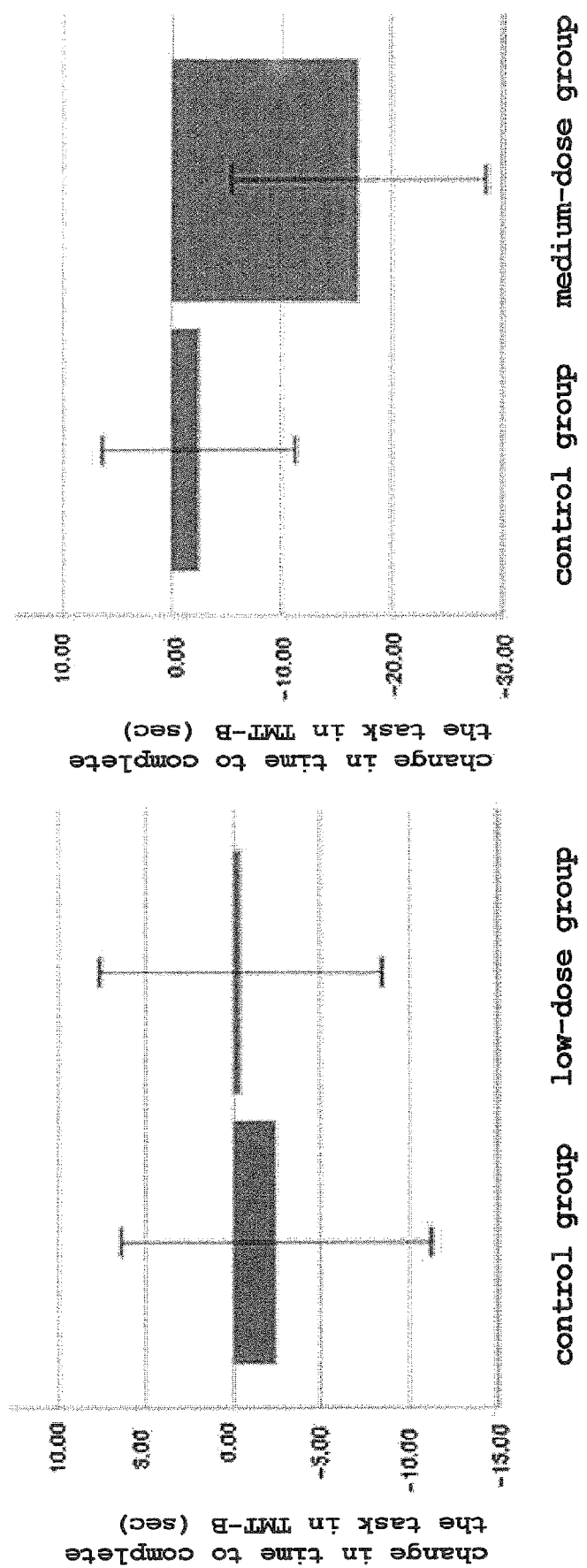
FIG. 8 shows the effects of the ingestion of the composition of Example 2 on the time to complete the task in the TMT-B test in Experimental Example 8. In the Figure, error bar shows 95% confidence interval.

The amount of change in TMT-B in each group, that is, the value obtained by subtracting the baseline value from the value after 12 weeks was calculated and shown in FIG. 8.

TMT-B was developed as a test to evaluate frontal lobe dysfunction, in which test the time to draw lines to connect numbers 1 to 13 and hiragana letters (Japanese syllabary letters) "A" to "Shi" alternating between numbers and hiragana letters in ascending order is measured. It is a test capable of particularly evaluating attention function, executive function (flexibility) and the like. Accordingly, the results of this test can be interpreted as the evaluation results of whether or not one can perform work efficiently in daily life and the like. Therefore, as the amount of change in TMT-B turns into a more negative value, it means that the attention function, executive function (flexibility) and the like have been improved more.

In FIG. 8, the mean value of TMT-B change (seconds) in the control food group (Placebo 1) is −2.44, and standard deviation is 25.77; the mean value of the test food low-dose group (Active 2) is −0.44, and standard deviation is 23.49; and the mean value of the test food medium-dose group (Active 1) is −17.00, and standard deviation is 33.20. An unpaired t-test was performed between Placebo 1 and each group of Active 1 and Active 2.

As a result, no significant difference was found between Placebo 1 and Active 2, but a significant difference (P=0.049) was found between Placebo 1 and Active 1.

From the above-mentioned results of Experimental Example 8, an intervention effect of the ingestion of the test food medium-dose was shown in, among the cognitive functions, attention function, executive function and the like in which the TMT-B test result becomes an index.

Therefore, it was suggested that the composition of the present invention is effective in improving a decline in cognitive function that does not lead to pathological cognitive dysfunction such as dementia, but is observed in healthy humans, for example, reduction in attention, decline in thinking skills, decline in working memory (function of temporarily storing and managing the information) and the like.

INDUSTRIAL APPLICABILITY

As described in detail above, a composition for improving cognitive function can be provided according to the present invention.

The composition for improving cognitive function of the present invention effectively improves cognitive function and is effective for preventing or improving various symptoms or disorders caused by a decline in cognitive function.

In addition, the composition for improving cognitive function of the present invention also functions as a composition for improving anxiety-like symptoms and is effective for preventing or reducing the expression of anxiety-like symptoms that appear along with a decline in cognitive function or before and after the decline of cognitive function.

Furthermore, the composition for improving cognitive function of the present invention also functions as a composition for suppressing cerebral atrophy and is effective for suppressing cerebral atrophy observed in neurodegenerative diseases such as Alzheimer-type dementia and the like, and physiological cerebral atrophy that appears and progresses with aging, and improving a decline in cognitive function caused by such cerebral atrophy.

Particularly, the composition for improving cognitive function of the present invention is highly safe and suitable for continuous ingestion or administration.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for improving cognitive function, comprising administering to a subject in need thereof a composition comprising the following amino acids at the following contents relative to the total content of leucine, lysine, valine, isoleucine, phenylalanine, histidine, and tryptophan:
   leucine 25 mol % to 45 mol %,
   phenylalanine 20 mol % to 40 mol %,
   lysine 10 mol % to 30 mol %,
   valine 2 mol % to 7 mol %,
   isoleucine 5 mol % to 15 mol %,
   histidine 2 mol % to 10 mol %, and
   tryptophan 0.1 mol % to 2 mol %.

2. A method for improving an anxiety-like symptom, comprising administering to a subject in need thereof a composition comprising the following amino acids at the following contents relative to the total content of leucine, lysine, valine, isoleucine, phenylalanine, histidine, and tryptophan:
   leucine 25 mol % to 45 mol %,
   phenylalanine 20 mol % to 40 mol %,
   lysine 10 mol % to 30 mol %,
   valine 2 mol % to 7 mol %,
   isoleucine 5 mol % to 15 mol %,
   histidine 2 mol % to 10 mol %, and
   tryptophan 0.1 mol % to 2 mol %.

3. A method for suppressing cerebral atrophy, comprising administering to a subject in need thereof a composition comprising the following amino acids at the following contents relative to the total content of leucine, lysine, valine, isoleucine, phenylalanine, histidine, and tryptophan:
   leucine 25 mol % to 45 mol %,
   phenylalanine 20 mol % to 40 mol %,
   lysine 10 mol % to 30 mol %,
   valine 2 mol % to 7 mol %,
   isoleucine 5 mol % to 15 mol %,
   histidine 2 mol % to 10 mol %, and
   tryptophan 0.1 mol % to 2 mol %.

4. The method according to claim 1, wherein the composition is a pharmaceutical product.

5. The method according to claim 1, wherein the composition is a food.

* * * * *